US008852095B2

(12) United States Patent
Schlottau et al.

(10) Patent No.: US 8,852,095 B2
(45) Date of Patent: Oct. 7, 2014

(54) HEADBAND FOR USE WITH MEDICAL SENSOR

(75) Inventors: Friso Schlottau, Lyons, CO (US); Sarah Hayman, Boulder, CO (US); Charles Haisley, Boulder, CO (US); Andy S. Lin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 286 days.

(21) Appl. No.: 13/283,217

(22) Filed: Oct. 27, 2011

(65) Prior Publication Data
US 2013/0104288 A1    May 2, 2013

(51) Int. Cl.
| | | |
|---|---|---|
| *A42B 1/24* | (2006.01) |
| *A61B 5/01* | (2006.01) |
| *A61B 5/02* | (2006.01) |
| *D04B 1/18* | (2006.01) |
| *A41D 1/00* | (2006.01) |
| *A41D 20/00* | (2006.01) |
| *A61B 5/00* | (2006.01) |
| *D04B 1/00* | (2006.01) |
| *A61B 5/1455* | (2006.01) |

(52) U.S. Cl.
CPC ............ *A61B 5/6831* (2013.01); *A61B 2505/03* (2013.01); *A61B 5/01* (2013.01); *A61B 5/02* (2013.01); *A61B 5/14551* (2013.01); *A61B 5/6803* (2013.01); *A61B 5/1455* (2013.01); *A61B 5/6814* (2013.01); *D04B 1/18* (2013.01); *A41D 20/00* (2013.01); *A41D 1/002* (2013.01)
USPC ........... 600/300; 600/323; 600/340; 600/372; 600/382; 600/383; 600/390; 2/171; 2/171.1; 2/171.2; 2/171.4; 2/171.5; 2/200.1; 66/169 R; 66/170; 66/171

(58) Field of Classification Search
CPC .. A61B 5/6831; A61B 5/6814; A61B 5/6803; A61B 5/1455; A61B 5/14551; A61B 5/02; A61B 5/01; A61B 2505/03; A41D 102/002; A41D 20/00; D04B 1/18
USPC ................ 600/340, 323, 372, 382, 383, 390; 2/171, 171.1, 171.2, 171.4–171.5, 2/200.1
See application file for complete search history.

(56) References Cited

U.S. PATENT DOCUMENTS 2,549,836 A * 4/1951 McIntyre et al. ............. 600/383
4,510,938 A * 4/1985 Jobsis et al. .................. 600/344
(Continued)

FOREIGN PATENT DOCUMENTS

| EP | 1986543 | 11/2008 |
|---|---|---|
| WO | 0028888 | 5/2000 |

OTHER PUBLICATIONS

Ceelen, K.K., et al., Compression-induced damage and internal tissue strains are . . . Journal of Biomechanics (2008), doi: 10, 1016/j.jbiomech.2008.09.016.

(Continued)

*Primary Examiner* — William Thomson
*Assistant Examiner* — Marie Archer
(74) *Attorney, Agent, or Firm* — Fletcher Yoder PC

(57) ABSTRACT

Headbands configured to provide pressure against a medical sensor secured to a patient's forehead are provided. The headbands may include one or more low friction materials to enable an elastic band of a tensioning mechanism to evenly stretch. Additionally or alternatively, the headbands may include two or more bands adapted to secure the headband to various portions of a patient's head. Still further, the headbands may be configured to independently vary the pressure created between two or more sensors and the patient's head.

19 Claims, 14 Drawing Sheets

(56) References Cited

U.S. PATENT DOCUMENTS

| | | | |
|---|---|---|---|
| 4,681,413 A | 7/1987 | Schmidt et al. | |
| 5,099,842 A | 3/1992 | Mannheimer et al. | |
| 5,295,490 A * | 3/1994 | Dodakian | 600/534 |
| 5,817,008 A | 10/1998 | Rafert et al. | |
| 5,919,133 A * | 7/1999 | Taylor et al. | 600/323 |
| 5,950,245 A | 9/1999 | Binduga | |
| 6,115,621 A | 9/2000 | Chin | |
| 6,171,258 B1 * | 1/2001 | Karakasoglu et al. | 600/529 |
| 6,343,223 B1 | 1/2002 | Chin et al. | |
| 6,525,386 B1 | 2/2003 | Mills et al. | |
| 6,671,531 B2 | 12/2003 | Al-Ali et al. | |
| 6,748,254 B2 | 6/2004 | O'Neil et al. | |
| 7,006,855 B1 | 2/2006 | Sarussi | |
| 7,047,055 B2 | 5/2006 | Boas et al. | |
| 7,047,056 B2 | 5/2006 | Hannula et al. | |
| 7,067,893 B2 | 6/2006 | Mills et al. | |
| 7,096,052 B2 | 8/2006 | Mason et al. | |
| 7,190,986 B1 | 3/2007 | Hannula et al. | |
| 7,190,987 B2 | 3/2007 | Lindekugel et al. | |
| 7,289,837 B2 | 10/2007 | Mannheimer et al. | |
| 7,296,305 B2 | 11/2007 | Ketterer et al. | |
| 7,324,841 B2 | 1/2008 | Reho et al. | |
| 7,359,741 B2 | 4/2008 | Sarussi | |
| 7,377,794 B2 | 5/2008 | Al-Ali et al. | |
| 7,440,788 B2 | 10/2008 | Jenkins et al. | |
| 7,483,731 B2 | 1/2009 | Hoarau et al. | |
| 7,574,245 B2 | 8/2009 | Arizaga Ballesteros | |
| 7,657,294 B2 | 2/2010 | Eghbal et al. | |
| 7,698,909 B2 | 4/2010 | Hannula et al. | |
| 7,721,349 B1 | 5/2010 | Strauss | |
| 7,809,420 B2 | 10/2010 | Hannula et al. | |
| 7,810,359 B2 | 10/2010 | Hannula et al. | |
| 7,813,779 B2 | 10/2010 | Hannula et al. | |
| 7,822,453 B2 | 10/2010 | Mannheimer et al. | |
| 7,877,126 B2 | 1/2011 | Hannula et al. | |
| 7,877,127 B2 | 1/2011 | Hannula et al. | |
| 7,880,884 B2 | 2/2011 | Medina | |
| 7,904,130 B2 | 3/2011 | Raridan | |
| 7,979,102 B2 | 7/2011 | Hannula et al. | |
| 8,071,935 B2 | 12/2011 | Besko et al. | |
| 8,257,274 B2 | 9/2012 | Medina | |
| 8,346,328 B2 | 1/2013 | Mannheimer et al. | |
| 8,352,004 B2 | 1/2013 | Mannheimer et al. | |
| 8,364,220 B2 | 1/2013 | Sandmore | |
| 2001/0027282 A1 * | 10/2001 | Baugh | 602/7 |
| 2004/0054291 A1 | 3/2004 | Schulz et al. | |
| 2004/0122302 A1 | 6/2004 | Mason et al. | |
| 2004/0221370 A1 * | 11/2004 | Hannula et al. | 2/181 |
| 2004/0267104 A1 | 12/2004 | Hannula et al. | |
| 2005/0059869 A1 | 3/2005 | Scharf et al. | |
| 2005/0070776 A1 | 3/2005 | Mannheimer et al. | |
| 2005/0197556 A1 * | 9/2005 | Stoler | 600/383 |
| 2005/0197579 A1 | 9/2005 | Baker et al. | |
| 2005/0283082 A1 * | 12/2005 | Geddes et al. | 600/485 |
| 2006/0020179 A1 | 1/2006 | Anderson et al. | |
| 2006/0058690 A1 * | 3/2006 | Bartnik et al. | 600/504 |
| 2006/0074283 A1 * | 4/2006 | Henderson et al. | 600/315 |
| 2006/0085891 A1 | 4/2006 | Larkin et al. | |
| 2006/0089547 A1 | 4/2006 | Sarussi | |
| 2006/0189871 A1 | 8/2006 | Al-Ali et al. | |
| 2006/0195028 A1 | 8/2006 | Hannula et al. | |
| 2006/0211922 A1 | 9/2006 | Al-Ali et al. | |
| 2006/0211923 A1 | 9/2006 | Al-Ali et al. | |
| 2006/0211924 A1 | 9/2006 | Dalke et al. | |
| 2006/0229509 A1 | 10/2006 | Al-Ali et al. | |
| 2006/0241363 A1 | 10/2006 | Al-Ali et al. | |
| 2006/0264722 A1 | 11/2006 | Hannula et al. | |
| 2006/0264723 A1 | 11/2006 | Hannula et al. | |
| 2006/0264724 A1 | 11/2006 | Hannula et al. | |
| 2006/0264725 A1 | 11/2006 | Hannula et al. | |
| 2006/0264726 A1 | 11/2006 | Mannheimer et al. | |
| 2006/0264727 A1 | 11/2006 | Mannheimer et al. | |
| 2006/0281984 A1 | 12/2006 | Mannheimer et al. | |
| 2007/0038050 A1 | 2/2007 | Sarussi | |
| 2007/0073125 A1 | 3/2007 | Hoarau et al. | |
| 2007/0078309 A1 | 4/2007 | Matlock | |
| 2007/0078311 A1 | 4/2007 | Al-Ali et al. | |
| 2007/0083094 A1 | 4/2007 | Colburn et al. | |
| 2007/0106134 A1 | 5/2007 | O'Neil et al. | |
| 2007/0142717 A1 | 6/2007 | Lowery et al. | |
| 2008/0216211 A1 | 9/2008 | Dolby | |
| 2008/0220633 A1 | 9/2008 | Al-Ali et al. | |
| 2008/0221463 A1 | 9/2008 | Baker | |
| 2009/0171177 A1 | 7/2009 | Hannula et al. | |
| 2010/0076276 A1 | 3/2010 | Gilland | |
| 2010/0076282 A1 | 3/2010 | Sandmore | |
| 2010/0081900 A1 | 4/2010 | Price | |
| 2010/0081904 A1 | 4/2010 | Medina | |
| 2010/0186211 A1 | 7/2010 | Macan et al. | |
| 2010/0186749 A1 | 7/2010 | Macan et al. | |
| 2010/0206323 A1 | 8/2010 | August | |
| 2010/0234706 A1 | 9/2010 | Gilland | |
| 2010/0249551 A1 | 9/2010 | Miller | |
| 2010/0249553 A1 | 9/2010 | MacLaughlin | |
| 2010/0249554 A1 | 9/2010 | McKenna et al. | |
| 2010/0249557 A1 | 9/2010 | Besko et al. | |
| 2010/0261995 A1 | 10/2010 | McKenna et al. | |
| 2010/0261996 A1 | 10/2010 | Li et al. | |
| 2010/0298678 A1 | 11/2010 | Klomhaus | |
| 2010/0327063 A1 | 12/2010 | Medina et al. | |
| 2010/0331631 A1 | 12/2010 | MacLaughlin | |
| 2011/0041232 A1 * | 2/2011 | Covelli et al. | 2/69 |
| 2011/0046464 A1 | 2/2011 | Debreczeny et al. | |
| 2011/0077483 A1 | 3/2011 | Boutelle | |
| 2011/0112379 A1 | 5/2011 | Li et al. | |
| 2011/0213226 A1 | 9/2011 | Miller et al. | |
| 2012/0071742 A1 | 3/2012 | Medina et al. | |
| 2012/0216335 A1 | 8/2012 | McKenna et al. | |
| 2012/0248985 A1 | 10/2012 | Lin et al. | |
| 2012/0253148 A1 | 10/2012 | Haisley et al. | |
| 2012/0253152 A1 | 10/2012 | Haisley et al. | |
| 2012/0253159 A1 | 10/2012 | Medina et al. | |

OTHER PUBLICATIONS

U.S. Appl. No. 13/328,619, filed Dec. 16, 2012, Charles K. Haisley.
U.S. Appl. No. 13/717,380, filed Dec. 17, 2012, Paul D. Mannheimer.
U.S. Appl. No. 61/013,850, filed Dec. 14, 2007, Carine Hoarau.
U.S. Appl. No. 13/239,666, filed Sep. 22, 2011, David P. Besko.
U.S. Appl. No. 13/239,681, filed Sep. 22, 2011, David P. Besko.
U.S. Appl. No. 13/239,700, filed Sep. 22, 2011, David P. Besko.
U.S. Appl. No. 13/248,733, filed Sep. 29, 2011, Friso Schlottau.

* cited by examiner

US 8,852,095 B2

HEADBAND FOR USE WITH MEDICAL SENSOR

BACKGROUND

The present disclosure relates generally to medical devices and, more particularly, to medical sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. These devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Pulse oximetry readings may involve placement of a sensor on a patient's tissue, such as via an adhesive sensor, a clip-style sensor, or a sensor that may be fitted into or against a wearable garment, such as a hat or a headband. With regard to the latter, if the hat or headband is not closely fitted to the patient's tissue, ambient light may interfere with the sensor's light detection. However, such a conforming fit may be difficult to achieve over a range of patient physiologies (e.g., head, arm, leg sizes) without periodic adjustment or excessive attention on the part of medical personnel. Additionally, the hat or headband may not remain accurately positioned during the entire time the patient is being monitored due to patient movement, diaphoresis, a loss or misapplication of tension of the hat or headband, or similar occurrences. Further, an overly tight fit may cause an undesired amount of local exsanguination of the tissue around the sensor. Exsanguinated tissue, which is devoid of blood, may shunt the sensor light through the tissue, resulting in reduced measurement accuracy.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
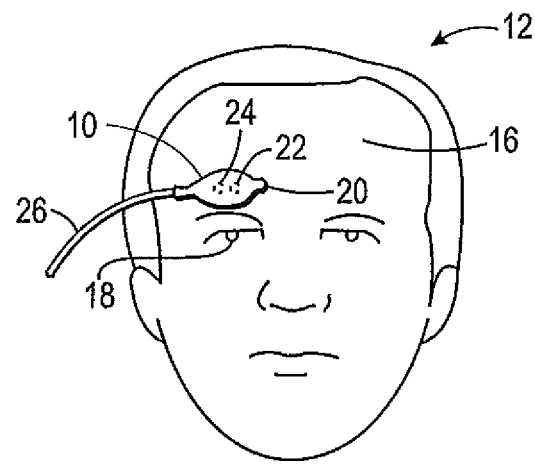
FIG. 1 is a diagram of an embodiment of a forehead pulse oximetry sensor being applied to a patient, in accordance with an aspect of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed above, medical sensors held against a patient tissue by a hat, headband, or other wearable garment can experience a loss in performance as a result of movement of the garment. Movement of the garment (e.g., a headband) during measurement may result from patient movement, misapplication of the headband, various physiological conditions such as diaphoresis, or a combination of these and/or similar factors. Accordingly, present embodiments include headbands and similar garments configured to reduce movement of the headband associated with these situations, resulting in enhanced sensor performance and increased patient comfort. It should be noted that while the embodiments of the present disclosure are discussed in the context of a headband, that similar garments, such as hats, visors, booties, socks, wristbands, armbands, chest bands, and the like, are also presently contemplated. Thus, the embodiments disclosed herein may be implemented on any such garment for use in combination with medical sensors that may benefit from the techniques disclosed herein.

Embodiments of the present disclosure provide headbands having features that may increase the reliability associated with applying the headbands at a desired tension. By ensuring an appropriate amount of tension provided by the headband, suitable pressure may be applied between a medical sensor held in place by the headband and underlying patient tissue. The suitable pressure may result in increased accuracy in the measurements performed by the medical sensor. Proper tensioning of the headband may also at least partially reduce the occurrence of headband slippage while providing a comfortable fit for the patient.

One manner by which accurate tensioning of the headband may be accomplished in accordance with the present disclosure includes reducing friction between various portions of the headband. Embodiments such as these are discussed below with respect to FIGS. 4-7. Other approaches, which may be used in combination with or in lieu of the embodiments discussed with respect to FIGS. 4-7, may include reducing the elasticity of a main headband material and modifying the stopping mechanism of an elastic band configured to set the tension of the headband. These approaches, which may also be used alone or in any combination, are discussed in detail with respect to FIGS. 8-13.

Figure 14:
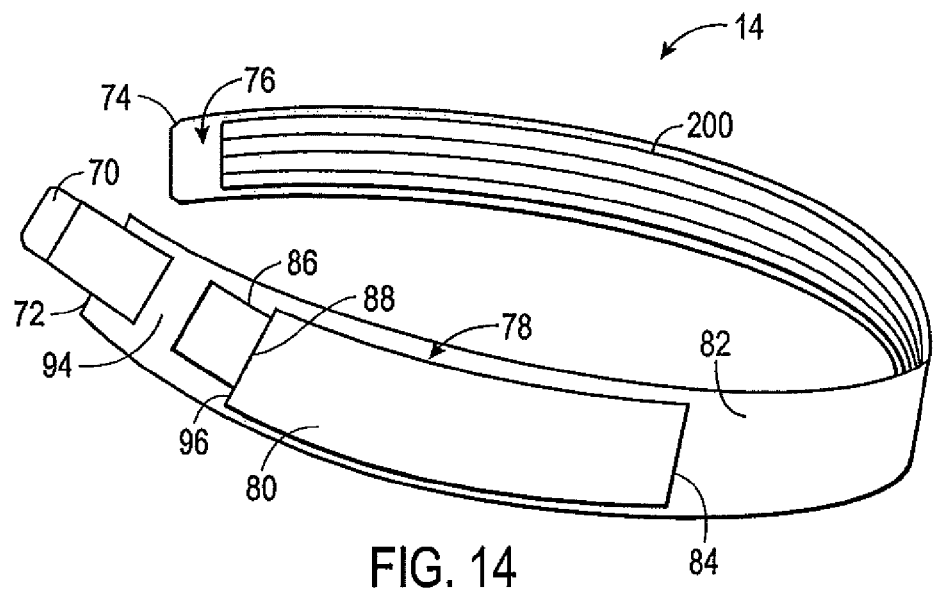
FIG. 14 is a perspective view of an embodiment of the headband of FIGS. 1-4 having a high friction strip lined on an inner surface of the headband, in accordance with an aspect of the present disclosure.
Figure 15A:
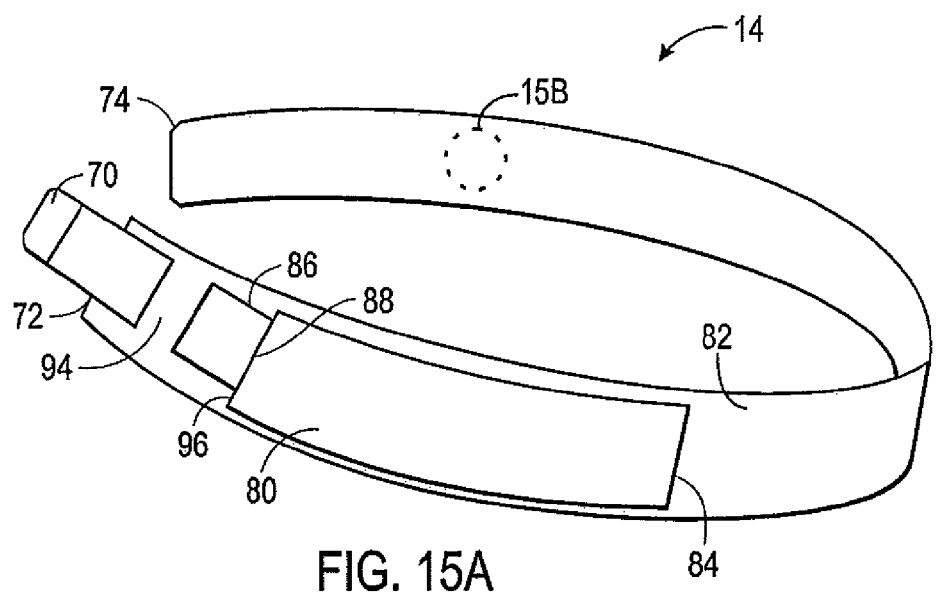
FIG. 15A is a perspective view of an embodiment of the headband of FIGS. 1-4, at least a portion of the headband including a microporous material that enables the evaporation of moisture, in accordance with an aspect of the present disclosure.

In addition to, or in lieu of, ensuring proper headband tensioning, it may be desirable to provide materials that increase the friction between the headband and the patient to maintain the headband's position on the patient. Accordingly, the present embodiments also provide headbands that may include materials configured to enhance or maintain friction between the headband and the patient. Such embodiments are discussed with respect to FIGS. 14 and 15. As noted above, any of the techniques or approaches described herein may be used in any combination. Accordingly, a non-limiting example of an embodiment of a headband combining different approaches for proper tensioning and reducing headband slippage is discussed with respect to FIG. 16. Providing additional bands adapted to secure the headband to different parts of the patient's head may also reduce slippage of the headband. For example, certain of the present embodiments provide headbands having one or more additional bands for wrapping around the top and/or bottom of a patient's head. Example embodiments of these headbands are discussed with respect to FIGS. 17-19.

The present embodiments also provide headbands configured to increase the comfort associated with wearing the headband in conjunction with one or more medical sensors, while simultaneously enabling the one or more sensors to accurately perform physiological measurements. For example, in situations where two or more sensors are held in place against the patient's forehead by a headband, it may be desirable to apply different levels of pressure for each sensor against the patient's forehead. Embodiments for providing different pressures, or for maintaining equal pressures, across two or more sensors are discussed below with respect to FIGS. 20-24.

Figure 2:
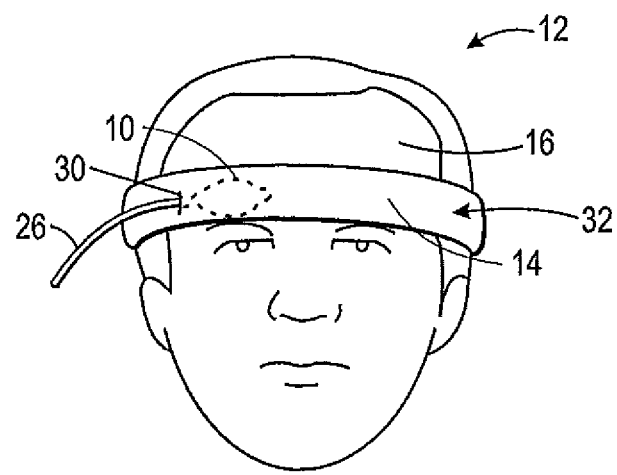
FIG. 2 is a diagram of the forehead pulse oximetry sensor of FIG. 1 being held against a patient's forehead using a headband, in accordance with an aspect of the present disclosure.

With the foregoing in mind, an example embodiment of the manner in which a sensor 10 may be positioned on a patient 12 and held in place by a headband 14 is illustrated with respect to FIGS. 1 and 2. As depicted, the sensor 10 is a pulse oximetry sensor configured to measure the concentration of certain constituents within the patient's blood. By way of example, the sensor 10 may be an OXIMAX™, NEOMAX™, or other pulse oximetry sensor available from Nellcor Puritan Bennett, LLC. Indeed, while the embodiments disclosed herein are presented in the context of pulse oximetry sensors, it should be noted that they may be applicable to any medical sensor held in place by a headband or other garment, such as those used for measuring hematocrit, water fraction, electroencephalographic measurements such as bispectral index (BIS), or other physiological parameters. Thus, the sensor 10 may be a part of a local or centralized monitoring system, as discussed below with respect to FIG. 3.

As illustrated in FIG. 1, the sensor 10 may be placed on the patient's forehead 16 in a desired location, such as above an eye 18. However, it should be noted that the sensor 10 may be placed in any region on the patient's body, such as another cerebral location or a somatic location, or a combination. For example, the sensor 10 may be placed on the patient's stomach, chest, back, or similar somatic location. In FIG. 1, a body 20 of the sensor 10, which houses an emitter 22 and a detector 24, is placed above the eye 18. The body 20 of the sensor 10 may include an adhesive or other gripping surface configured to secure the sensor 10 to the patient's skin. As discussed in further detail below, the emitter 22 and the detector 24 are configured to use one or more wavelengths of light to aid in the determination of various blood oxygen parameters. The emitter 22 and the detector 24 are each connected to a cable 26 configured to relay signals to and from the emitter 22 and the detector 24.

Once the sensor 10 is positioned on the patient 12, the headband 14 may be placed around the patient's head to press the sensor 10 against the patient's forehead 16, as shown in FIG. 2. The headband 14 may have a tension setting such that when the headband 14 is suitably applied, a desired level of pressure is created between the sensor 10 and the patient's forehead 16. The tension may be set in a number of ways, examples of which are discussed below with respect to FIGS. 9-13. In some embodiments, the desired tension may be such that variations in measurements performed by the emitter 22 and the detector 24 due to venous pulsations are reduced, and exsanguination of the tissue of the forehead 16 located between the emitter 22 and the detector 24, which may cause light shunting, is prevented. Conversely, as noted above, overtensioning the headband 14 may lead to discomfort for the patient 12.

The headband 14 may also include an opening 30 to enable the cable 26 to pass over an outer surface 32 of the headband 14, which may also increase comfort for the patient 12. For example, in configurations where the cable 26 is disposed between the headband 14 and the patient 12, the headband 14 may press the cable 26 against the patient's forehead 16, which may be uncomfortable for the patient 12 over extended periods of time. Thus, it may be desirable to route the cable 26 through the opening 30 to reduce or eliminate the pressure caused by the cable 26.

Figure 3:
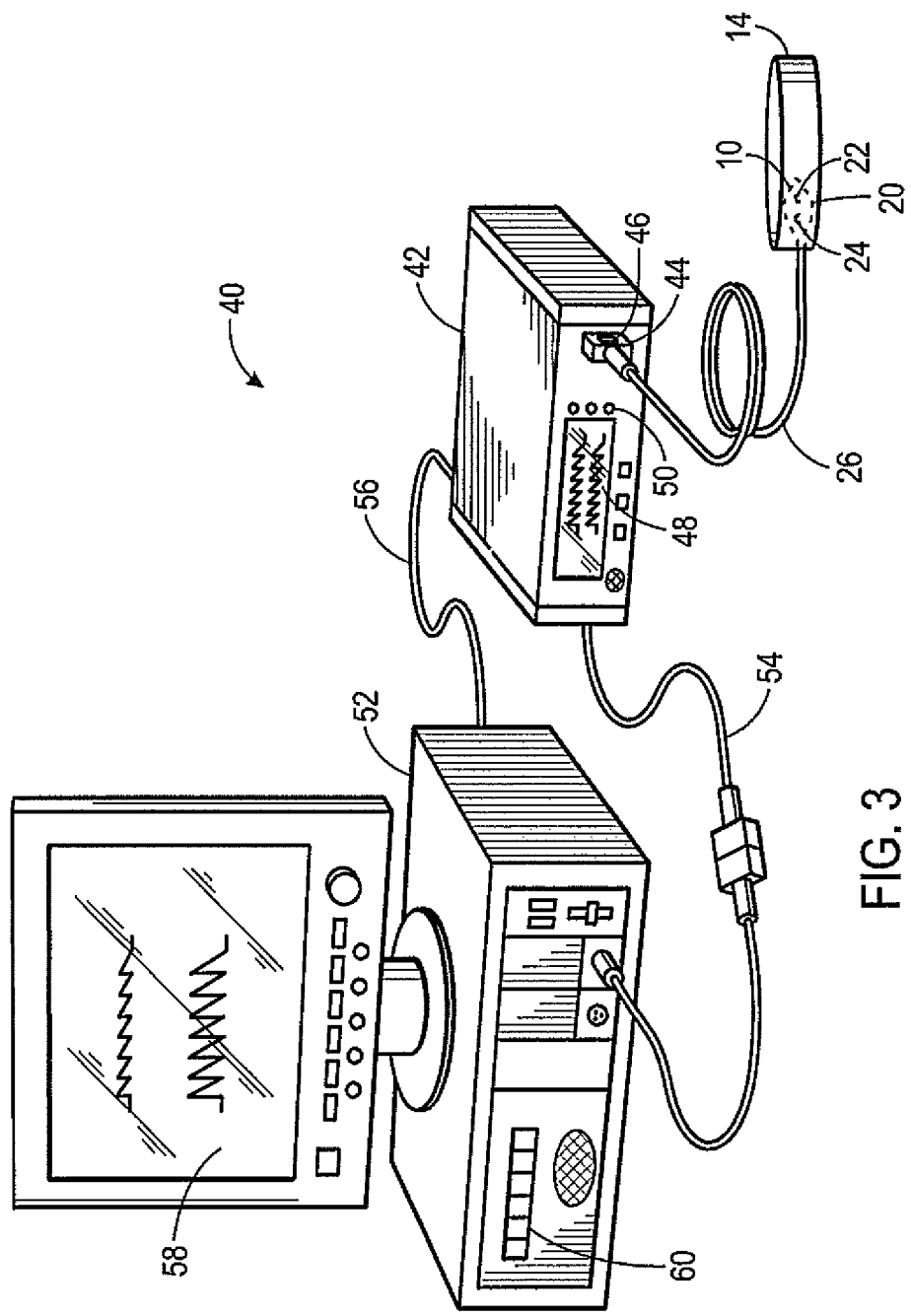
FIG. 3 is a perspective view of an embodiment of a patient monitoring system configured to monitor one or more physiological parameters of a patient, and including an embodiment of the forehead oximetry sensor and the headband of FIGS. 1 and 2, in accordance with an aspect of the present disclosure.

The cable 26 may route signals between the sensor 10 and one or more patient monitors, as noted above. FIG. 3 depicts one embodiment of a patient monitoring system 40 that is configured to perform pulse oximetry and other physiological measurements, and may be used in conjunction with the sensor 10. Although the depicted embodiments relate to sensors for use on a patient's head, it should be understood that, in certain embodiments, the features of the sensor 10 as provided herein may be incorporated into sensors for use on other tissue locations, such as the back, the stomach, the heel, an arm, a leg, or any other appropriate measurement site over which a garment may be placed. In addition, although the embodiment of the patient monitoring system 40 illustrated in FIG. 3 relates to photoplethysmography or pulse oximetry, the system 40 may be configured to obtain a variety of medical measurements with a suitable medical sensor. For example, the system 40 may additionally or alternatively be configured to determine patient electroencephalography (e.g., a bispectral index), or any other desired physiological parameter such as water fraction or hematocrit.

The system 40 includes the sensor 10, which may be disposed in the headband 14, and is communicatively coupled to a patient monitor 42. The emitter 22 and detector 24 of the sensor 10 are coupled to the monitor 42 via the cable 26. The cable 26 couples the sensor 10 to the monitor 42 using a connector 44 configured to interface with a sensor port of the monitor 42. The cable 26 may interface directly with the sensor 10 and may include a plurality of conductors surrounded by an insulating material. In certain embodiments, the cable 26 may include a relatively flat, flexible cable, such as a ribbon cable or a flexible circuit using copper, silver, or gold (e.g., via a printable metal ink) on a dielectric substrate, such as a KAPTON® polyimide dielectric substrate. While the illustrated cable 26 couples to the monitor 42 via the connector 44, it should be noted that in some embodiments, the sensor 10 and associated cable 26 may couple to a pre-amplifier (not shown) configured to amplify signals collected by the detector 24. For example, the pre-amplifier may have a cable that couples to the cable 26 and additional cable that couples to the monitor 42. However, in the illustrated embodiment, the pre-amplifier may be provided as a part of the monitor 42. The connector 44, in certain embodiments, may include a memory unit 46 that may be configured to store patient historical data, such as historical oximetry data. The memory unit 46, alternatively or additionally, may be configured to store sensor-related information and time-out functionality to facilitate the operability of the sensor 10 with the monitor 42. In some embodiments, the memory unit 46 may be an erasable programmable read-only memory (EPROM) or write once, read many (WORM) memory having code configured to execute a time-out routine that disables the operability of the sensor 10 with the monitor 42 after a predetermined number of connections and/or uses, or after a predetermined amount of time.

The monitor 42 includes a monitor display 48 configured to display information regarding the physiological parameters monitored by the sensor 10, information about the system, and/or alarm indications. The monitor 42 may include various input components 50, such as knobs, switches, keys and keypads, buttons, etc., to provide for operation and configuration of the monitor. The monitor 42 also includes a processor that may be used to execute code such as code for implementing various monitoring functionalities enabled by the sensor 10. For example, in combination with the illustrated sensor 10 and headband 14, the monitor 42 may be configured to process signals generated by the detector 24 to estimate the amount of oxygenated vs, de-oxygenated hemoglobin in a cerebral region of the patient.

The monitor 42 may be any suitable monitor, such as a pulse oximetry monitor available from Nellcor Puritan Bennett, LLC. Furthermore, to upgrade conventional operation provided by the monitor 42 to provide additional functions, the monitor 42 may be coupled to a multi-parameter patient monitor 52 via a cable 54 connected to a sensor input port or via a cable 56 connected to a digital communication port. In addition to the monitor 42, or alternatively, the multi-parameter patient monitor 52 may be configured to calculate physiological parameters and to provide a central display 58 for the visualization of information from the monitor 42 and from other medical monitoring devices or systems. The multi-parameter monitor 52 includes a processor that may be configured to execute code. The multi-parameter monitor 52 may also include various input components 60, such as knobs, switches, keys and keypads, buttons, etc., to provide for operation and configuration of the a multi-parameter monitor 52. In addition, the monitor 42 and/or the multi-parameter monitor 52 may be connected to a network to enable the sharing of information with servers or other workstations.

The sensor 10, illustrated as operatively connected to the monitor 42, may include the sensor body 20 that houses the emitter 22 for emitting light at certain wavelengths into a tissue of the patient 12 and the detector 24 for detecting the light after it is reflected and/or absorbed by the blood and/or tissue of the patient 12. The sensor body 20 may be formed from any suitable material, including rigid or conformable materials, such as fabric, paper, rubber, padded, foam, or elastomeric compositions (including acrylic elastomers, polyimide, silicones, silicone rubber, celluloid, PMDS elastomer, polyurethane, polypropylene, acrylics, nitrile, PVC films, acetates, and latex).

In certain embodiments, the sensor 10 may be a wireless sensor 10. Accordingly, the wireless sensor 10 may establish a wireless communication with the patient monitor 42 and/or the multi-parameter patient monitor 52 using any suitable wireless standard. By way of example, the wireless module may be capable of communicating using one or more of the ZigBee standard, WirelessHART standard, Bluetooth standard, IEEE 802.11x standards, or MiWi standard. Accordingly, in embodiments where the sensor 10 is configured for wireless communication, the cable 26 may be eliminated, increasing comfort and mobility for the patient 12 when wearing the headband 14.

Figure 4:
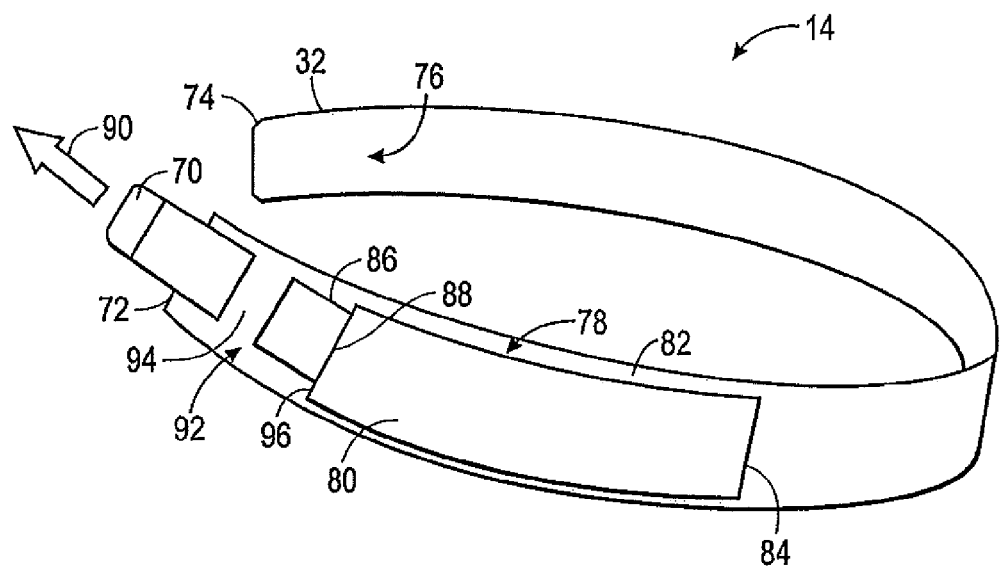
FIG. 4 is a perspective view of an embodiment of the headband of FIGS. 1-3 and including a main headband portion, a closure mechanism, and an elastic band to set the tension of the headband, in accordance with an aspect of the present disclosure.

As noted above, the headband 14 may include features that enable its use with a variety of patient anatomies to provide a comfortable fit while providing suitable pressure for the sensor 10. FIG. 4 depicts one embodiment of the headband 14, which includes a closure mechanism 70 configured to couple a first end 72 of the headband 14 with a second end 74 of the headband 14. Specifically, the second end 74 is positioned underneath the first end 72 such that an inner surface 76 of the headband 14 contacts the patient 12. The closure mechanism 70 interacts with the outer surface 32 at an area proximate the second end 74 to close the headband 14 around the patient's head. In accordance with present embodiments, the closure mechanism 70 may include a hook and loop (HAL) closure mechanism, hook-and-eye closure mechanism, snaps, buttons, adhesives, pins, hooks combined with cutouts in the headband 14, or any combination thereof. The closure mechanism 70, and its relation to setting the tension of the headband 14, is discussed in further detail below with respect to FIGS. 9-13.

The headband 14 also includes a tensioning mechanism 78, which may include an elastic band 80 attached to a main headband portion 82 at a first end 84 and to a relatively non-elastic band 86 at a second end 88. The tensioning mechanism 78 may be activated when the non-elastic band 86 is pulled in a direction generally away from the first end 72, as illustrated by arrow 90. Thus, when the non-elastic band 86 is pulled in direction 90, the elastic band 80 stretches and imparts a tension force to the headband 14. As previously noted, the tension force is used to apply a downward force, or pressure, on the sensor 10 against the patient's forehead 16 to eliminate variations in pulse oximetry measurements due to venous pulsations and patient movement. As discussed herein, this force is referred to as the normal force provided by the headband 14.

A hard stop 92 may at least partially limit the tension provided to the headband 14 by the tensioning mechanism 78. The hard stop 92 is configured to prevent the elastic band 80 from stretching beyond a certain point, effectively limiting the amount of tension that the elastic band 80 is able to provide. In the illustrated embodiment, the hard stop 92 is formed by a loop 94 through which the non-elastic band 86 is threaded and an abutment surface 96 of the elastic band 80. Specifically, the elastic band 80 is sufficiently large such that the abutment surface 96 is unable, during the normal course of operation and without interference, to pass through the loop 94, thus forming the hard stop 92. In another embodiment, a relatively non-flexible loop of fabric may be positioned under the elastic band 80. For example, the non-flexible loop may be attached to the elastic band 80 and the main headband portion 82, or may connect two or more different portions of the elastic band 80. The non-flexible loop may have a preset amount of slack built in. As the elastic is tensioned, the non-flexible loop would come taut, forming the hard stop 92.

While the tensioning mechanism 78 and the hard stop 92 are generally configured to control the amount of tension provided to the headband 14, in practice it may be difficult to reliably set the tension of the headband 14 and thus, the normal force applied provided by the headband 14. For example, certain factors that may contribute to the normal force may include the patient's head size (i.e., the extent to which portions of the headband 14 overlap, if at all), the patient's hair length, user application error, and the materials of the headband 14, to name a few. Furthermore, the normal force may be most predictable when the tension is set using only the elastic band 80. Unfortunately, the ability of the main headband portion 82 to stretch, even to a slight extent, as well as the friction forces between the components of the headband 14, can lead to inaccurate tension settings. For example, the normal force applied by the headband 14 may be a function of the elastic stretch distance of the elastic band 80, the elastic stretch distance of the main headband portion 82, the frictional force between overlapping portions of the headband 14 (e.g., between the first and second ends 72, 74), the frictional force between the elastic band 80 and the main headband portion 82, or any combination thereof. In embodiments where the patient's head is sufficiently large such that no overlap is created in the headband 14, the frictional forces between overlapping portions of the headband may not be a consideration.

By way of example, as the elastic band 80 is stretched, friction forces between the elastic band 80 and the main headband portion 82 may cause portions of the elastic band 80 to stick or catch on the main headband portion 82. This may cause uneven stretching of the elastic band 80, resulting in an incorrect tension setting for the headband 14. Thus, when a user (e.g., a caregiver) applies the headband 14 to the patient 12, the elastic band 80 may stick to the main headband portion 82 and subsequently slip as a result of movement or relaxation of the headband materials, causing de-tensioning of the headband 14 and subsequent movement of the headband 14, increasing the likelihood of inaccurate measurements by the sensor 10. In certain situations, the elastic band 80 may stick to the main headband portion 82, causing uneven stretching in the elastic band 80. This may cause higher than expected tension, which can result in inaccurate measurements and discomfort for the patient. Similarly, friction between the first and second ends 72, 74 may cause the first and second ends 72, 74 to catch or stick, causing the headband 14 to have a tension setting that may be reduced once the first and second ends 72, 74 slip over time or as a result of patient and/or headband movement.

To mitigate these frictional forces and to enable even stretching of the elastic band 80, the headband 14 may include one or more low friction materials. For example, in the embodiment illustrated in FIG. 4, the main headband portion 82 may be formed from or may include low friction materials such as a siloxane-coated low friction high density polyethylene (HDPE), fluoropolymers such as polytetrafluoroethylene (PTFE), or other low friction polymeric, metallic, semi-metallic, or similar materials. In one example embodiment, the main headband portion 82 may be formed from or may include TYVEK® high density polyethylene film or fabric available from E.I, duPont de Nemours and Co., which includes fibers that consist essentially of HDPE, and are randomly distributed and non-directional. In such embodiments, the low coefficient of friction between the elastic band 80 and the main headband portion 82 may be such that the elastic band 80 does not stick or catch during tension setting, which may increase the reliability of tension setting and headband application. That is, the elastic band 80 is able to evenly stretch without catching or sticking on the main headband portion 82. Similarly, the low coefficient of friction between the first and second ends 72, 74 may prevent any substantial sticking or catching during headband placement. Furthermore, in embodiments where the main headband portion 82 is formed from these or similar materials, the headband 14 may be relatively or completely non-elastic, which may also facilitate accurate tension setting.

Figure 5:
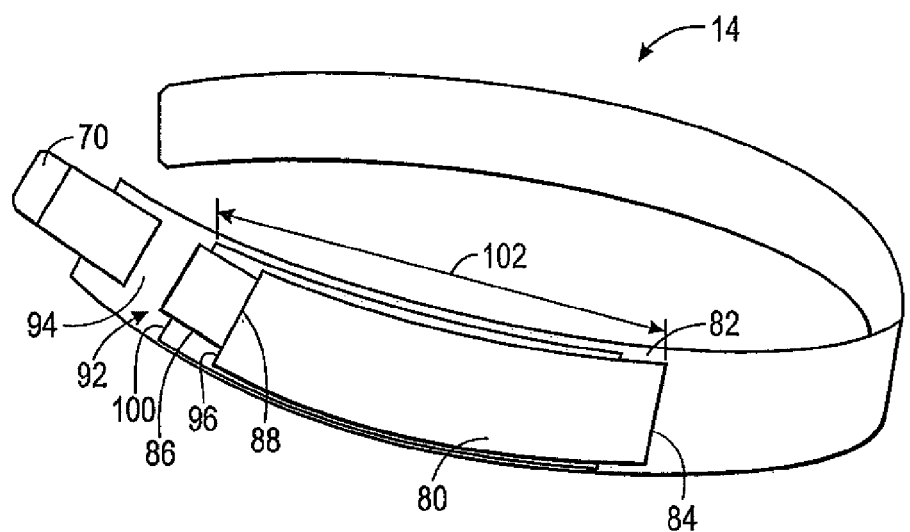
FIG. 5 is a perspective view of an embodiment of the headband of FIGS. 1-4 and including a low friction strip to enable even stretching of the elastic band for setting the tension of the headband, in accordance with an aspect of the present disclosure.

In addition to, or in lieu of, forming the main headband portion 82 from a low friction material, it may be desirable to provide a low friction strip 100 between the elastic band 80 and the main headband portion 82, as illustrated in FIG. 5. The low friction strip 100 may be adhered or otherwise fixed to the main headband portion 82, and may include any low friction material suitable or approved for use in medical contexts. As an example, the low friction strip 100 may be a polymeric strip that has been treated with a non-stick or low friction coating, such as a silicone-treated polymer strip. In one embodiment, the low friction strip 100 may be a silicone-treated HDPE film. The low friction strip 100 may be provided in a size that facilitates movement of the elastic band 80 along the main headband portion 82 without any substantial amount of sticking, catching, or other similar friction-induced mechanisms by which the elastic band 80 would unevenly stretch. For example, the low friction strip 100 may lie between the loop 94 and the first end 84 of the elastic band 80, and may span between approximately 50% and 100% of a total length 102 between the loop 94 and the first end 84, such as between approximately 60% and 90% or 70% and 80% of the length 102. Furthermore, the strip 100 may be positioned in the approximate center of the length 102, or may be offset toward the loop 94 or the first end 84. In this way, the low friction strip 100 facilitates proper tension setting for the headband 14 by enabling the elastic band 80 to evenly stretch (i.e., stretch along its entirety without bunching) without catching or sticking on the main headband portion 82.

Figure 6:
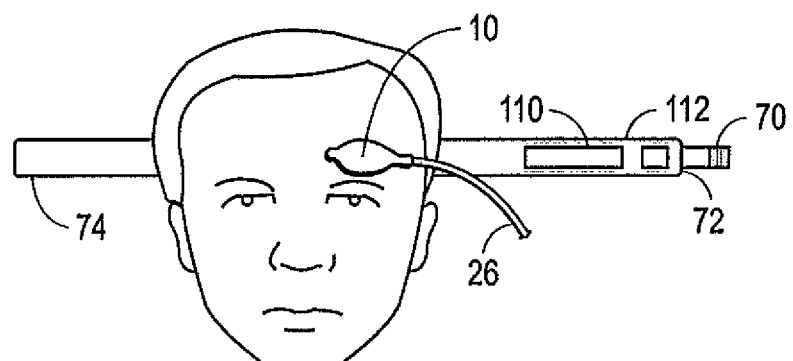
FIG. 6 is a front view of an embodiment of the headband of FIGS. 1-4 being applied to a patient, the headband having a low friction material to reduce friction between overlapping portions of the headband during and after application, in accordance with an aspect of the present disclosure.
Figure 7:
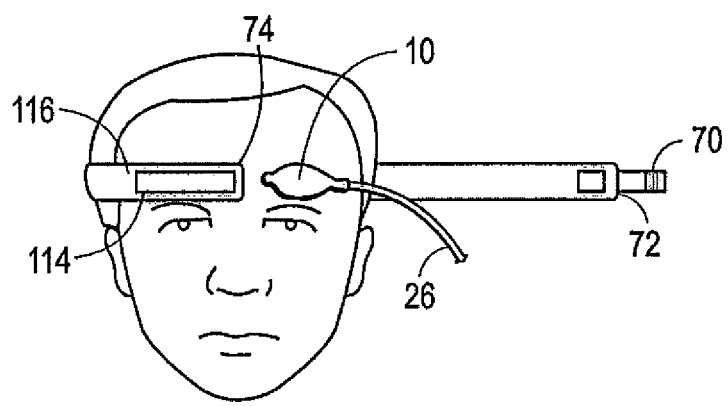
FIG. 7 is a front view of an embodiment of the headband of FIGS. 1-4 being applied to a patient, the headband having a low friction material to reduce friction between overlapping portions of the headband during and after application, in accordance with an aspect of the present disclosure.

Reducing the friction between the main headband portion 82, such as the first and second ends 72, 74, may also aid in tension setting of the headband 14. Indeed, in addition to or in lieu of providing the low friction strip 100, one or more low friction strips may be provided at either or both of the first and second ends 72, 74, as illustrated in FIGS. 6 and 7. However, it should be noted that the embodiments discussed with respect to FIGS. 6 and 7 are also applicable to embodiments in which the headband 14 is formed from low friction materials. Specifically, FIG. 6 depicts the sensor 10 in its proper positioning to perform pulse oximetry measurements on the forehead 16 of the patient 12. The headband 14 is depicted as being positioned, but not yet secured around the patient's head. As illustrated, the headband 14 includes a low friction strip 110 positioned in an overlap region 112 of the first end 72 of the headband 14. That is, the low friction strip 110 is placed in a region of the headband 14 where the first and second ends 72, 74 may overlap. The low friction strip 110 enables the first and second ends 72, 74 to move against one another without any substantial catching, sticking, or the like. As noted, such a reduction in friction enhances the reliability of positioning the headband 14 and setting the headband 14 to an appropriate tension. Similarly, a low friction strip 114 may be positioned in an overlap region 116 of the second end 74 of the headband 14, as illustrated in FIG. 7. Thus, low friction strips may be applied to respective overlap regions 112, 116 of the first and/or second ends 72, 74 to facilitate accurate tension setting of the headband 14. Again, these configurations may also occur in situations where the headband 14 is constructed from low friction materials. In such configurations, the low friction strips 110, 114 may not be present.

Figure 8:
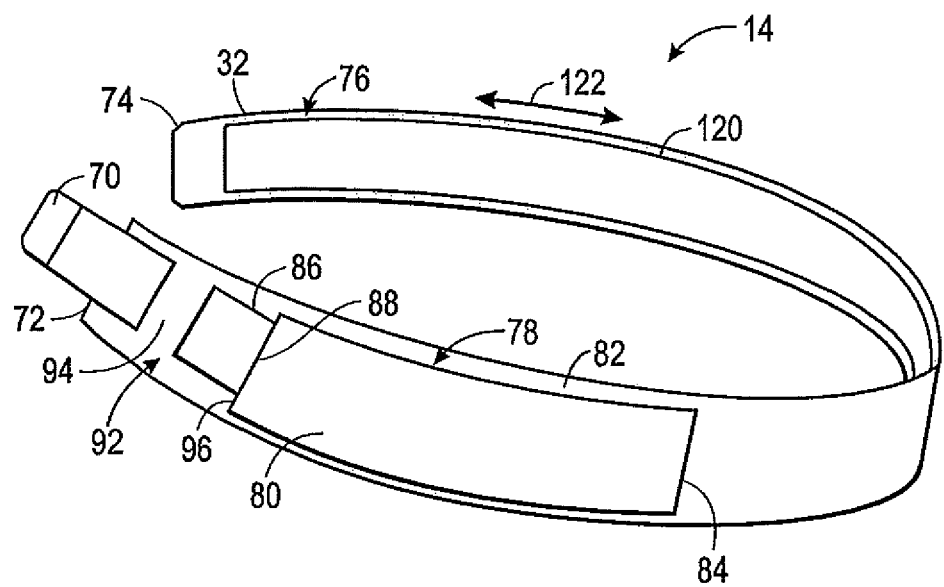
FIG. 8 is a perspective view of an embodiment of the headband of FIGS. 1-4 and including a non-elastic material to limit stretching of the headband, in accordance with an aspect of the present disclosure.

As noted above, the normal force applied by the headband 14 may be a function of the elastic stretch distance of the elastic band 80, the elastic stretch distance of the main headband portion 82, the frictional force between overlapping portions of the headband 14 (e.g., between the first and second ends 72, 74), the frictional force between the elastic band 80 and the main headband portion 82, or any combination thereof. While the low friction strips 100, 110, and 114, and embodiments in which the headband 14 includes or is constructed from a low-friction material address the friction forces associated with the headband 14 and the ability of the elastic band 80 to reliably stretch, the inherent elasticity of the main headband portion 82 may still create uncertainty with regard to the overall fit of the headband 14. Therefore, in accordance with an embodiment, a non-elastic strip 120 may be secured (e.g., adhered, stitched) to the inner surface 76 of the headband 14, as illustrated in FIG. 8. Indeed, in some embodiments, the main headband portion 82 and, in certain of these embodiments, the entire headband 14 other than the elastic band 80 may be formed from a non-elastic material. Therefore, while the discussion below is presented in the context of including the non-elastic strip 120, it should be noted that the present disclosure also contemplates embodiments in which the materials of the non-elastic strip 120 are incorporated into the main headband portion 82.

The non-elastic strip 120 may be formed from any material having an elasticity that is lower than the inherent elasticity of the main headband portion 82 (i.e., in embodiments where the main headband portion 82 has at least some degree of inherent elasticity). For example, in embodiments where the main headband portion 82 is a wool, cloth, or similar material, the non-elastic strip 120 may be a fibrous material, such as a low-stretch polyethylene, polyamide, polyester, polyether, siloxane, or other material. In an embodiment, the non-elastic strip 120 may be a strip of TYVEK® HDPE film. The non-elastic strip 120 may extend across the entire inner surface 76 of the headband 14, or only along a portion of the inner surface 76. In certain embodiments, it may be desirable for the non-elastic strip 120 to extend across between approximately 25 and 100%, such as approximately 25, 50, or 75% of a length 122 of the inner surface 76 to reduce the overall elasticity of the main headband portion 82. The non-elastic strip 120 may be substantially centered along the length 122, or may be offset toward either of the first or second ends 72, 74.

In addition to or in lieu of the non-elastic strip 120 being positioned on the inner surface 76, the non-elastic strip 120 may be positioned on the outer surface 32 of the headband 14. For example, in some embodiments, the non-elastic strip 120 may cover a portion of the outer surface 32 from the second end 74 to the first end 84 of the elastic band 80. In other embodiments, the non-elastic strip 120 may cover a substantial portion of the length 122 of the main headband portion 82 (e.g., between approximately 50% and 100%, or 70% and 90% of the length 122). In certain of these embodiments, the non-elastic strip 120 may be positioned between the main headband portion 82 and the tensioning mechanism 78. Again, in addition to or in lieu of the non-elastic strip 120 being positioned on the inner surface 76, the headband 82 may be made of an inelastic material to eliminate or reduce the possibility of stretching and relaxing of the headband.

In addition to having a relatively low elasticity compared to the main headband material 82, the non-elastic strip 120 may also serve as a friction-reducing surface. For example, as the first end 72 is positioned over the second end 74 during headband placement, the non-elastic strip 120 may serve a similar function to the low friction strips 112, 114. Thus, the non-elastic strip 120, in certain embodiments, may reduce sticking, catching, or the like as the ends 72, 74 move relative to one another.

While friction forces between certain materials of the headband 14 may introduce some uncertainty with regard to the actual tension of the headband 14, other factors, such as the movement of the closure mechanism 70, may affect the tension of the headband 14, and thus the normal force provided by the headband 14, as well. Accordingly, certain embodiments of the present disclosure provide approaches to mitigate the effect of movement of the closure mechanism 70 on the actual normal force provided by the headband 14. FIGS. 9-13 illustrate example embodiments of such approaches.

Figure 9A:
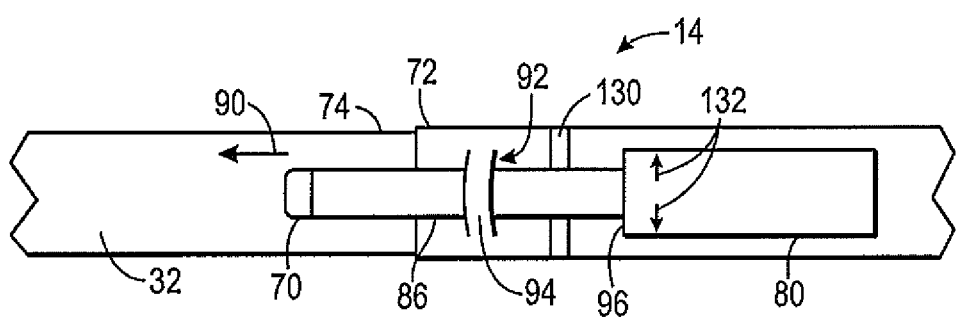
FIG. 9A is a front view of an embodiment of a hook and loop fastener and tension setting mechanism of the headband of FIGS. 1-4, in accordance with an aspect of the present disclosure.
Figure 9B:
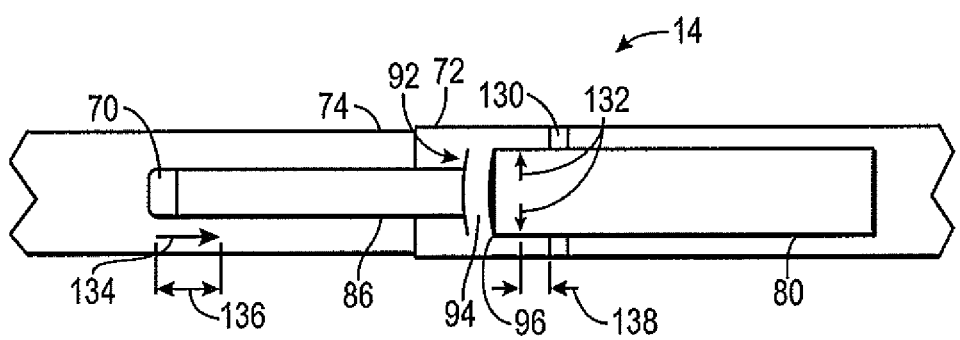
FIG. 9B is a front view of the embodiment of the hook and loop fastener and tension setting mechanism of FIG. 9A after initial tension setting and closure of the headband, in accordance with an aspect of the present disclosure.
Figure 9C:
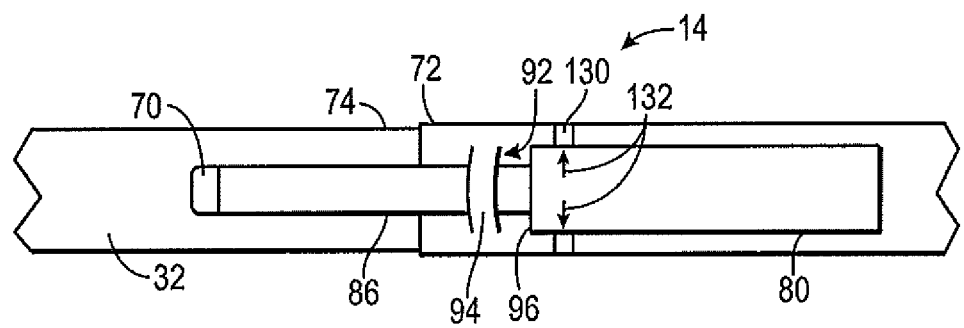
FIG. 9C is a front view of the embodiment of the hook and loop fastener and tension setting mechanism of FIG. 9B after relaxation of the closure mechanism and concomitant de-tensioning of the headband, in accordance with an aspect of the present disclosure.

Specifically, FIGS. 9A-9C illustrate an embodiment of the headband 14 that is configured to account for a certain amount of relaxation of the closure mechanism. For example, in embodiments where the closure mechanism 70 includes a HAL fastener or a similar fastening mechanism, the closure mechanism 70 may relax after initial closure of the headband 14, which reduces the tension of the headband 14. That is, the elastic spring force of the elastic band 80 at a maximum tension setting may be greater than the closure force of the closure mechanism 70. Accordingly, the actual tension of the headband 14 after such relaxation may be less than desired based upon the initial positioning of the closure mechanism 70. Therefore, in accordance with present embodiments, the headband 14 is initially over-tensioned by a desired amount. The closure mechanism 70 is subsequently allowed to relax, which de-tensions the headband 14 to a desired tension setting. Indeed, the over-tensioning of the headband 14 may be done to an extent that offsets the amount of relaxation of the closure mechanism 70.

In FIG. 9A, the headband 14 is illustrated in a configuration that would result from positioning the second end 74 on the patient 12, wrapping the headband 14 around the patient 12, and positioning the first end 72 over the second end 74. As illustrated, the headband 14 includes a stationary tension range indicator 130, depicted as parallel lines, and a moving tension indicator 132, depicted as arrows. In the configuration of FIG. 9A, the moving tension indicator 132 is to the right of the stationary tension range indicator 130, indicating that there is insufficient tension on the headband 14 for proper patient monitoring.

The closure mechanism 70 is pulled in direction 90 to tension the headband 14, and the closure mechanism 70, which in the illustrated embodiment may include a hook portion of a HAL fastener, is secured to the outer surface 32 of the headband 14, which may act as the loop portion of the HAL fastener. The resulting configuration is illustrated in FIG. 9B. As illustrated, the moving tension indicator 132 is positioned to the left of the stationary tension indicator 130, indicating that the headband 14 is over-tensioned. Additionally, the abutment surface 96 of the elastic band 80 is positioned against the loop 94, preventing the headband 14 from being further tensioned. In other words, in the illustrated embodiment, the headband 14 is fully tensioned at the hard stop 92. However, other configurations in which the headband 14 is initially tensioned to less than maximum tension are also presently contemplated.

As noted, the closure mechanism 70 may relax by a certain amount, indicated as arrow 134. In accordance with present embodiments, a distance 136 by which the closure mechanism 70 relaxes may be sufficient so as to de-tension the headband 14 to where the moving tension indicator 132 on the elastic band 80 moves to within the stationary tension range indicator 130. For example, the distance 136 may be substantially equal to or greater than a distance 138 between the moving tension indicator 132 and an outermost portion of the stationary tension range indicator 130. By way of example, the distance 136 may be between approximately 1 and 3 millimeters (mm), such as approximately 1, 2, or 3 mm, depending on the particular density of the HAL fastener. The configuration resulting from the relaxation of the closure mechanism 70 is illustrated in FIG. 9C.

The distance 136 resulting from the relaxation 134 may depend, for example, on a density of the HAL fastener. The density of the HAL fastener may represent the number of hook fasteners in a given area of the closure mechanism 70. As the number of hook fasteners per unit area increases, the density of the HAL fastener may increase. Further, the distance 136 resulting from the relaxation 134 may be tailored by adjusting the density of the HAL fastener, with higher densities resulting in reduced distance 136 of relaxation 134 and lower densities resulting in increased distance 136 of relaxation 134.

While relaxation of the closure mechanism 70 may be mitigated using the approaches described above, other factors may contribute to incorrect tensioning. Indeed, it may be a difficult task for a caregiver or similar personnel to apply the headband 14 such that the moving tension indicator 132 is within the stationary tension range indicator 130, especially in situations where the patient 12 is restless or uncooperative. Thus, in accordance with certain embodiments of the present disclosure, the tensioning mechanism 78 may be configured such that the tension of the headband 14 may be quickly adjusted while maintaining precision and accuracy. To enable such adjustment, a clasp or clip 150 may be provided to bunch the elastic band 80, as illustrated in FIG. 10A.

Figure 10A:
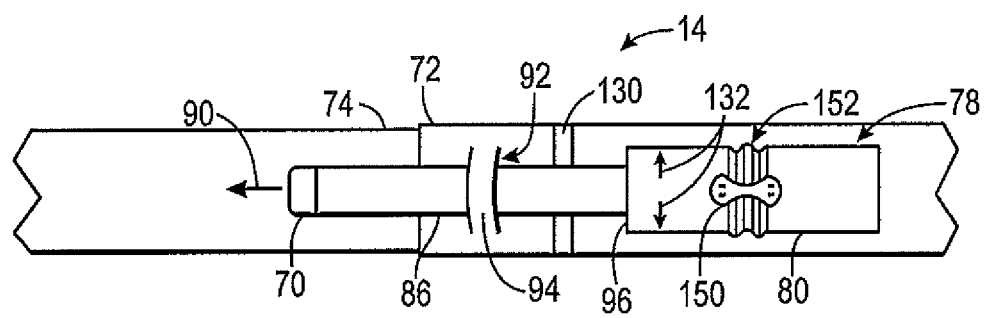
FIG. 10A is a front view of an embodiment of a hook and loop fastener and a pre-tensioned tension setting mechanism of the headband of FIGS. 1-4, in accordance with an aspect of the present disclosure.
Figure 10B:
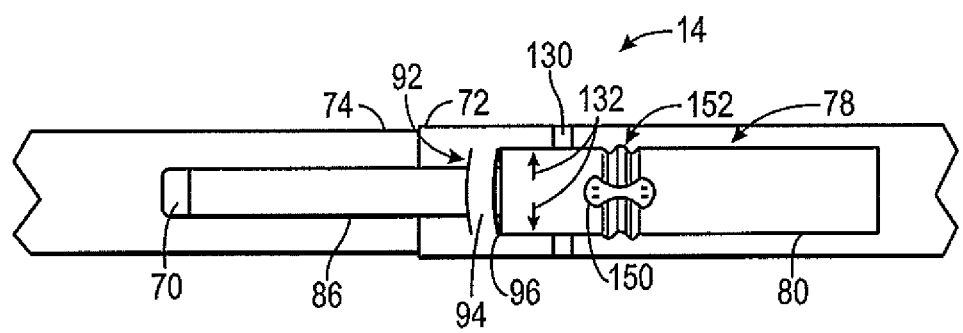
FIG. 10B is a front view of the embodiment of the hook and loop fastener and the pre-tensioned tension setting mechanism of FIG. 10A after initial tension setting and closure of the headband, in accordance with an aspect of the present disclosure.
Figure 10C:
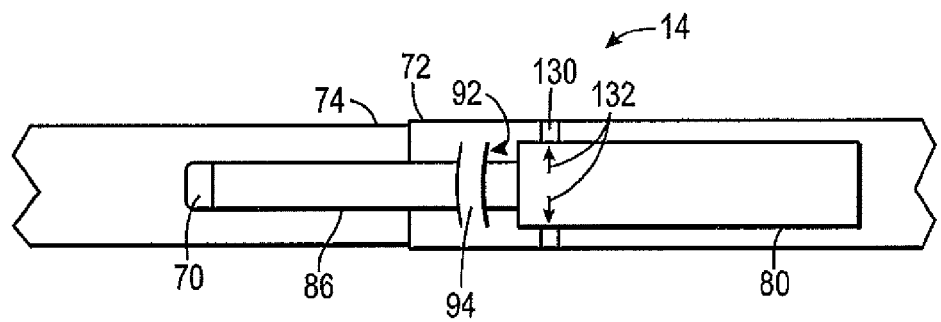
FIG. 10C is a front view of the embodiment of the hook and loop fastener and the tension setting mechanism of FIG. 10B after the pre-tensioning clip of the tension setting mechanism has been released to de-tension the headband to an appropriate tension setting, in accordance with an aspect of the present disclosure.

Specifically, as illustrated in FIG. 10A, the clip 150 may create folds 152 in the elastic band 80, which increases the resistance of the elastic band 80 by reducing its available elastic stretch distance. In this way, the clip 150 pre-tensions the elastic band 80. In operation, the caregiver may pull the closure mechanism 70 in the direction 90 until the abutment surface 96 contacts the loop 94, which is the hard stop 92. As illustrated in FIG. 10B, the resulting configuration is such that the moving tension indicator 132 is beyond the stationary tension range indicator 130, which is indicative of over-tensioning. The clip 150 is then released, enabling the elastic band 80 to have an increased stretch distance and reducing the tension of the headband 14. Accordingly, as depicted in FIG. 10C, the moving tension indicator 132 is positioned within the stationary tension indicator range 130, and the elastic band 80 is substantially free of any folds 152.

In the embodiment described above with respect to FIGS. 10A-10C, it should be noted that it may be desirable for the closure mechanism 70 to undergo little to no movement after securing. Accordingly, the present disclosure also provides various approaches, described with respect to FIGS. 11-13, for increasing the strength by which the headband 14 is secured using the closure mechanism 70. Thus, the embodiments described with respect to FIGS. 11-13 may be used in conjunction with any of the approaches described herein, for example the embodiments described above with respect to FIGS. 4-8 and 10A-10C.

Figure 11A:
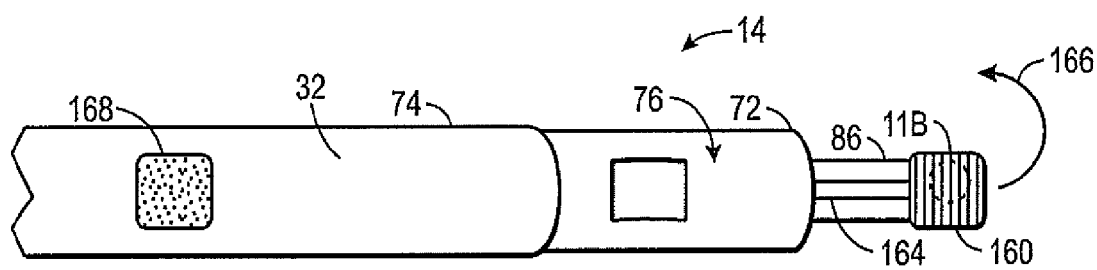
FIG. 11A is a front view of an embodiment of the headband of FIGS. 1-4 having a hook and loop fastener closure mechanism disposed on one end of the headband, and a corresponding mating surface on another end of the headband, in accordance with an aspect of the present disclosure.
Figure 11B:
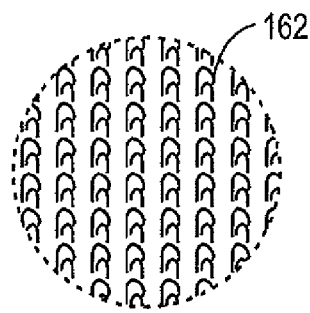
FIG. 11B is an expanded view of the hook and loop fastener of FIG. 11A illustrating a plurality of hooks having varying orientations, in accordance with an aspect of the present disclosure.

As noted above, in certain embodiments, the closure mechanism 70 may include closures that are configured to undergo little to no movement upon closure of the headband 14. One such embodiment of the closure mechanism 70 is illustrated in FIG. 11A, where the headband 14 includes a hook and loop (HAL) fastener 160 having a density that is sufficient to prevent any substantial movement of the closure mechanism 70 upon closure of the headband 14. As defined herein, no substantial movement of the closure mechanism 70 is intended to denote a situation in which the tension of the headband 14 does not undergo a discernable change. The discernable change may be observed by a change in the position of the moving tension indicator 132. An expanded view of the HAL fastener 160 is provided in FIG. 11B, which depicts a plurality of hooks 162 oriented in random or alternating directions. Such a configuration may enable the HAL fastener 160 to have a secure attachment to its corresponding attachment surface.

The HAL fastener 160 is directly secured to the non-elastic band 86, and is attached to the first end 72 of the headband 14 by an elastic tether 164. The elastic tether 164 is generally configured to ensure that the first end 72 of the headband 14 is pulled taut during tensioning and closure of the headband 14. As illustrated, the HAL fastener 160 may be routed over the second end 74 of the headband 14 in a direction 166, represented as an arrow, toward a mating surface 168. In certain embodiments, the mating surface 168 may be the material of the headband (which may be a fabric material), a reusable adhesive patch, or a loop portion of the HAL fastener. In embodiments where the mating surface 168 is an additional piece separate from the main headband portion 82, the mating surface 168 may be secured to the main headband portion 82 via an adhesive or a HAL fastener. For example, in embodiments where the main headband portion 82 is formed from a material that is a low friction material (i.e., a material that is inappropriate for direct attachment to a HAL fastener), the mating surface 168 may be secured to the main headband portion 82 via an adhesive or stitching. Thus, the mating surface 168 may be movable with respect to the main headband portion 82 in certain embodiments.

Figure 12:
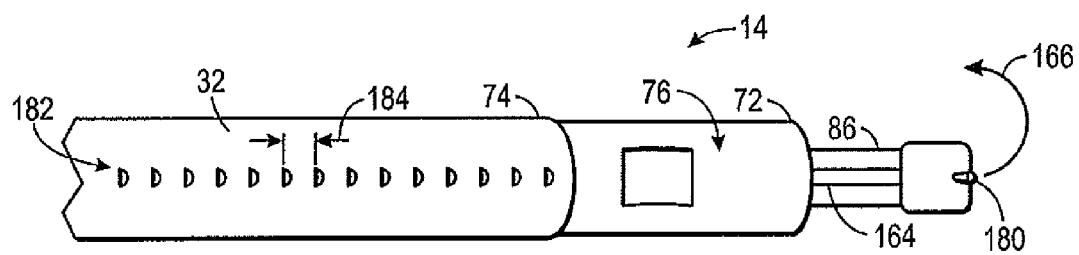
FIG. 12 is a front view of an embodiment of the headband of FIGS. 1-4 having a hook and a plurality of eyelets as a closure mechanism, wherein each of the eyelets are formed directly into the headband, in accordance with an aspect of the present disclosure.
Figure 13:
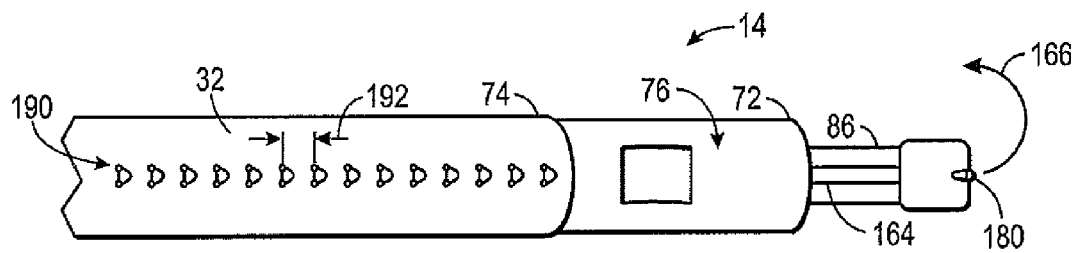
FIG. 13 is a front view of an embodiment of the headband of FIGS. 1-4 having a hook and a plurality of eyelets as a closure mechanism, wherein each of the eyelets are attached to the headband, in accordance with an aspect of the present disclosure.

In addition to or in lieu of a HAL fastener, the headband 14 may include a hook closure 180 configured to loop through one or more eyelets 182 formed in the main headband portion 82. Such an embodiment is illustrated in FIG. 12, and includes a plurality of the eyelets 182 formed in the outer surface 32 of the headband 14. The eyelets 182 may each be spaced from one another by a distance 184 that enables the headband 14 to be worn by a variety of patients having different anatomies. As an example, the distance 184 between each of the eyelets 182 may be between approximately 0.5 and 3 centimeters (cm) apart, such as approximately 1, 2, or 2.5 cm apart. Indeed, in one embodiment the particular eyelet 182 chosen for a given patient may be determined based upon which eyelet 182 positions the moving tension indicator 132 within the stationary tension range indicator 130. Furthermore, the size and shape of the eyelets may be configured such that they lie substantially flat on the headband 14. Such a configuration may be desirable to reduce the possibility of producing significant pressure on the patient's head as it rests on a pillow (e.g., in a hospital bed)

In a similar embodiment, the headband 14 may include eyelets 190 that are a different material than the main headband portion 82. For example, the eyelets 190 may be the same material as the hook fastener 180, such as a metallic material, or may be a felt, a polymer, or a similar material that is able to withstand repeated use. The eyelets 190 may be adhesively secured, or may be secured by stitching, gluing, curing, or similar processes. As with the eyelets 182 described above, the eyelets 190 may be spaced by a distance 192 that enables the headband 14 to be worn by a variety of patients having different anatomies. The distance 192 between each of the eyelets 182 may be between approximately 0.5 and 3 centimeters (cm) apart, such as approximately 1, 2, or 2.5 cm apart. As above, the particular eyelet 190 chosen for a given patient may be determined based upon which eyelet 190 positions the moving tension indicator 132 within the stationary tension range indicator 130.

As discussed above, the fit of the headband 14 on the patient 12, as well as the ability of the headband 14 to provide a suitable normal force on the sensor 10 and the patient's forehead 16 may be determined by the tensioning of the headband 14, as discussed above, as well as the ability of the headband 14 to stay in place on the patient 12. For example, in certain embodiments, the headband 14 may be configured such that if the normal force that the headband 14 exerts on the patient's head is sufficient to repel lateral forces exerted on the headband 14 as the patient moves, the headband 14 will stay in place. However, the amount of lateral force sufficient for overcoming the normal force to cause slippage of the headband 14 may be reduced as the friction between the headband 14 and the patient 12 is reduced. Factors that may reduce this friction include long hair, secretions such as sweat and oil, low tension, and so forth. Accordingly, as described with respect to FIGS. 14-19, the present embodiments include approaches for preventing slippage of the headband 14 by providing materials that are configured to increase the friction between the headband 14 and the patient 12 and additional straps for enabling a secure fit.

One approach for increasing the friction between the headband 14 and the patient 12 in accordance with present embodiments is to provide a high friction or gripping material on the inner surface 76 of the headband 14. An embodiment of such a configuration is illustrated with respect to FIG. 14, which depicts the headband 14 as having a high friction lining 200 attached to the inner surface 76 of the main headband portion 82. The high friction lining 200 may be formed from or may include any high friction material that is suitable or approved for use in medical devices. As an example, the high friction lining 200 may be a rubber or other elastomeric lining configured to provide a relatively high coefficient of friction between the patient 12 and the headband 14. Further, the high friction lining 200 may enable the headband 14 to remain positioned even in situations where the patient 12 has long hair, sweats excessively, or other conditions which would otherwise reduce the ability of the headband 14 to remain properly positioned.

Figure 15B:
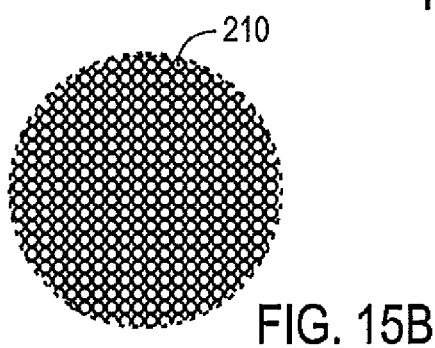
FIG. 15B is an expanded view of the microporous material of the headband of FIG. 15A, in accordance with an aspect of the present disclosure.
Figure 16:
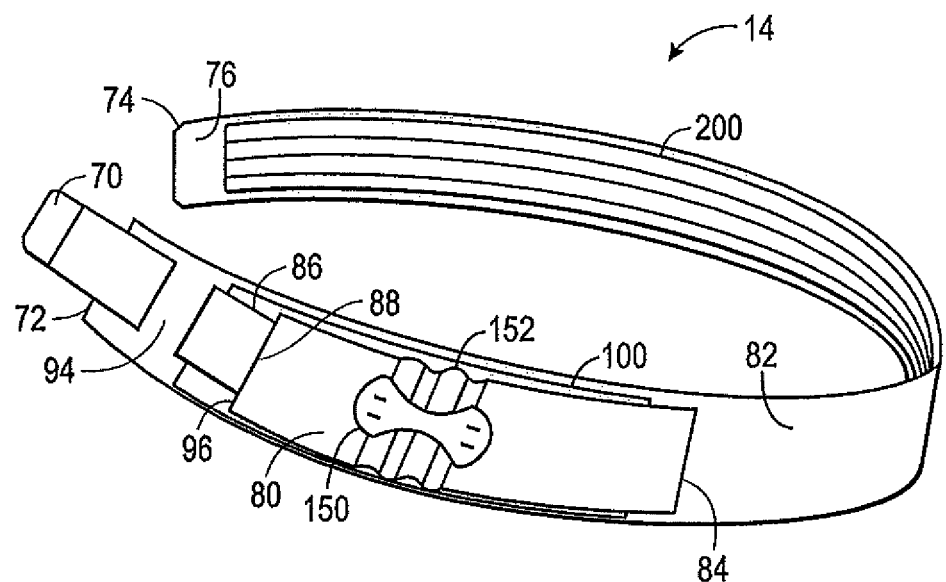
FIG. 16 is a perspective view of an embodiment of the headband of FIGS. 1-4 having a low friction strip in accordance with the embodiment of FIG. 5, a pre-tensioned elastic band in accordance with the embodiment of FIGS. 10A and 10B, and a high friction strip in accordance with the embodiment of FIG. 14, in accordance with an aspect of the present disclosure.

In addition to, or in lieu of, providing high friction materials on the inner surface 76, the headband 14 may include or be formed from a microporous material that enables moisture (e.g., sweat) to evaporate away from the patient-headband interface. One embodiment in which the headband 14 includes microporous materials is illustrated with respect to FIGS. 15A and 15B. Indeed, the headband main portion 82 may be formed from the microporous material, which may be a porous polymer such as PTFE or a similar fluoropolymer. An expanded view of the main headband portion 82 is illustrated in FIG. 15B. As depicted, the main headband portion 82 includes a plurality of pores 210 each having a size that enables moisture evaporation while preventing water passage. As an example, the headband 14 may be formed from GORE-TEX® porous fabric available from W.L. Gore and Associates, Inc. In such embodiments, the pores 210 may each be approximately five orders of magnitude smaller than a water droplet.

Therefore, the main headband portion 82 may be formed from a porous fluoropolymer that, in addition to enabling moisture wicking to maintain headband positioning on the patient 12, may also reduce the friction between the first and second ends 72, 74 of the headband 14 and between the elastic band 80 and the main headband portion 82. Accordingly, the inclusion of GORE-TEX® or similar materials in the main headband portion 82 may prevent headband slippage while concomitantly enabling proper tension setting in accordance with the embodiments described above with respect to FIGS. 4 and 5. It should be noted that in certain embodiments, the microporous material (e.g., GORE-TEX fabric) may be included in the main headband portion 82 in only discrete areas, such that the main headband portion 82 contains areas formed from a traditional headband fabric such as cotton, polyester, nylon, or the like, and areas that are formed from the microporous material.

Again, any one or a combination of the approaches may be used together in the headband 14. An example embodiment of one combination is illustrated with respect to FIG. 16. The illustrated headband 14 includes the low friction strip 100, which enables the elastic band 80 to stretch without catching or sticking to the underlying material of the main headband portion 82. The headband 14 also includes the clip 150, which is configured to form folds 152 in the elastic band 80 to pre-tension the elastic band 80 to enable quick and accurate tension setting. Further, the headband 14 includes the high friction lining 200, which is provided on the inner surface 76 of the headband 14 for increasing the coefficient of friction between the patient 12 and the headband 14.

Figure 17:
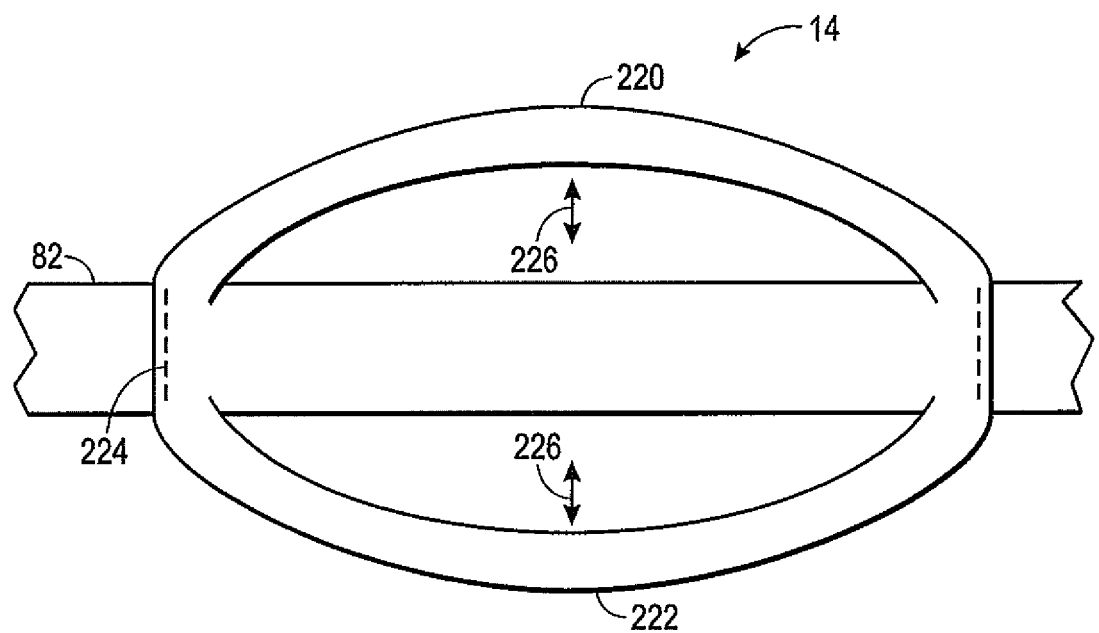
FIG. 17 is a front view of an embodiment of the headband of FIGS. 1-4 having additional bands for securing the headband to the patient's head over a plurality of regions, in accordance with an aspect of the present disclosure.
Figure 18:
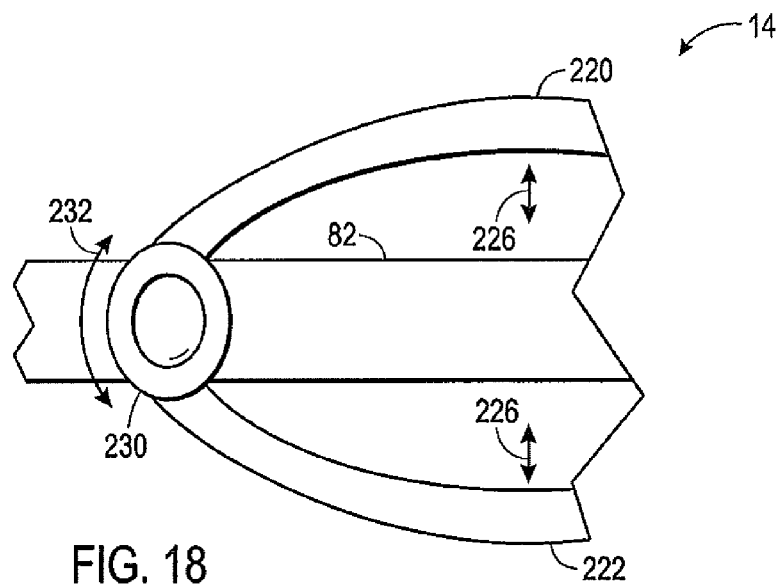
FIG. 18 is a front view of an embodiment of the headband of FIGS. 1-4 having additional bands for securing the headband to the patient's head over a plurality of regions, in accordance with an aspect of the present disclosure.
Figure 19:
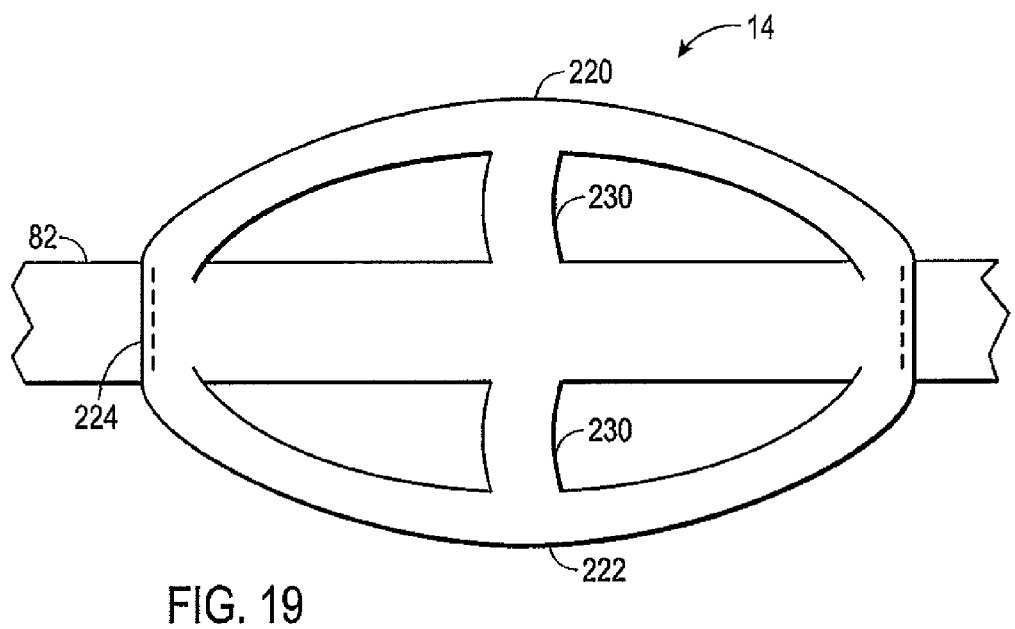
FIG. 19 is a front view of an embodiment of the headband of FIGS. 1-4 having additional bands for securing the headband to the patient's head over a plurality of regions, in accordance with an aspect of the present disclosure.
Figure 20:
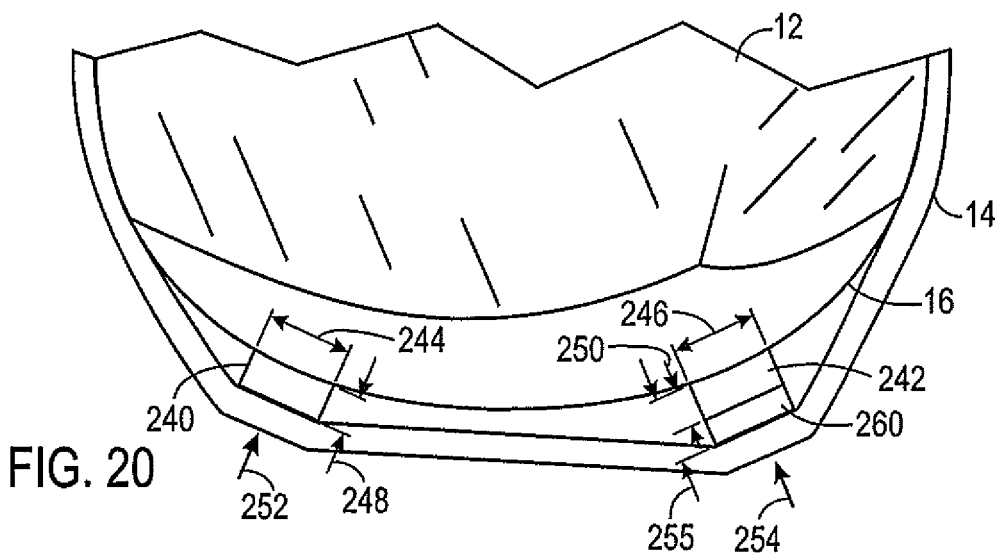
FIG. 20 is a top view of an embodiment of the headband of FIGS. 1-4 and illustrated as securing two sensors to a patient, the sensors and the headband being configured to provide different pressures against the patient's forehead by providing a different thickness for the sensors, in accordance with an aspect of the present disclosure.

The positioning of the headband 14 on the patient 12 may also be maintained by providing additional contact area between the headband 14 and the patient 12. For example, as illustrated in FIGS. 17-19, certain embodiments of the headband 14 may include one or more additional straps that are configured to secure the headband 14 to different areas of the patient's head. In FIG. 17, the headband 14 includes first and second additional bands 220, 222 that are fixedly secured at each end 224 to the main headband portion 82 of the headband 14.

The first additional band 220 may be configured to wrap around a top portion of the patient's head, while the second additional band 222 may be configured to cup the backside of the patient's head. In this way, the illustrated headband 14 having the first and second additional bands 220, 222 cups the patient's head, which provides stability to the headband 14, and also enables accurate positioning of the headband 14 and increased comfort for the patient 12.

As illustrated, the first and second additional bands 220, 222 are sewn to the main headband portion 82. However, in other embodiments the first and second additional bands 220, 222 may be secured to the main headband portion 82 by a clasp, adhesive, HAL fasteners, buttons, hook and eye fasteners, or similar securing method. Because the first and second additional bands 220, 222 are only attached to the main headband portion 82 at their ends 224, they may have some degree of freedom to move toward and away from the main headband portion 82, as illustrated by arrows 226. Indeed, this freedom of movement may enable the headband 14 to be worn by patients having various head sizes. Further, in embodiments where less than all of the three bands (i.e., the main headband portion 82 and the first and second additional bands 220, 222) are desired for use, the first additional band 220, or the second additional band 222, or both, may be positioned directly in line with the main headband portion 82.

To enable an even greater freedom of movement, as illustrated in FIG. 18, the first and second additional bands 220, 222 may be secured to the main headband portion 82 using a pivot 230. The pivot 230 may be directly attached to the main headband portion 82, and may rotatably couple the first and second additional bands 220, 222 to the main headband portion 82. The pivot 230 may be a plastic, metallic, or composite pivot joint or similar feature that in addition to allowing movement in the direction 226, also enables the bands 220, 222 to rotatably move, as illustrated by arrow 232. Thus, the pivot 230 enables the headband 14 to conform to a variety of patient head sizes while ensuring a snug fit for each of the bands 82, 220, 222 to the patient 12.

It should be noted that while the headbands 14 discussed with respect to FIGS. 17 and 18 include two additional bands, that any number of additional bands are presently contemplated. For example, the headband 14 may use either of the first or second additional bands 220, 222, or may utilize the first and second additional bands 220, 222 as well as additional bands. Indeed, the headband 14 may utilize one or more bands in addition to the first and second additional bands 220, 222. By way of example, the headband 14 may include one or more additional crosswise bands 230 that are oriented crosswise with respect to the first and second additional bands 220, 222, as illustrated in FIG. 19. The additional crosswise bands 230 may provide additional contact area between the patient 12 and the headband 14, while also maintaining the relative positioning of the first additional band 220, the second additional band 222, and the main headband portion 82. As discussed above with respect to FIGS. 17 and 18, the additional crosswise bands 230 may be secured to the first and second additional bands 220, 222 by stitching, a clasp, adhesive, HAL fasteners, buttons, hook and eye fasteners, or similar securing methods, or by a pivot joint as illustrated in FIG. 18.

While the embodiments described above are presented in the context of using the headband 14 in conjunction with a single sensor, such as a pulse oximetry sensor, it may be desirable to use the sensor 10 in conjunction with another medical sensor. Non-limiting examples of additional medical sensors that may be used include an additional pulse oximetry sensor, an EEG sensor (e.g., a bispectral index (BIS) sensor), other optical and acoustical sensors such as a photon density wave sensor, a photoacoustic sensor, a regional oximetry sensor, or any medical sensor configured to measure a physiological parameter such as hematocrit, water fraction, or the like. However, it should be noted that the use of multiple sensors may be difficult due to pressure variations for each sensor. For example, when two sensors are used, such as a first and a second sensor, it may be desirable to apply differing amounts of pressure to each to facilitate accurate measurement. The pressure suitable for accurate measurement may be determined based on the type of each sensor, as well as the dimensions of each sensor. For example, a suitable pressure for a forehead pulse oximetry sensor may not be the same as a suitable pressure for a BIS sensor. Embodiments for providing different pressures in such situations, which may be used alone or in combination with the embodiments described above with respect to FIGS. 4-19, are described below with respect to FIGS. 20-22.

In situations where two or more sensors are utilized that each have different contact areas with the patient's forehead 16, it may be desirable to apply similar pressures for each. Accordingly, present embodiments include approaches, which may be used alone or in combination with the embodiments described above with respect to FIGS. 4-19, for providing similar pressures across multiple sensors, as discussed with respect to FIG. 23. Additionally, in situations where the headband 14 is configured for use with a particular sensor, such as the sensor 10, the headband 14 may be configured to have a pocket or other relief for holding the sensor 10 in place, while enabling use of the headband 14 with only the sensor 10, or with the sensor 10 and any of the additional sensors mentioned above. Furthermore, in certain embodiments, various sensing components, such as the emitter 22 and the detector 24, may be integrated into the headband 14 for providing pressure relief, while simultaneously enabling the use of the headband 14 in conjunction with any one or a combination of the additional sensors. Such embodiments, which may be used alone or in any combination with the embodiments described above with respect to FIGS. 4-23, are described with respect to FIG. 24.

As noted above, various physiological sensors may be accuracy dependent on pressure. Accordingly, an embodiment of an approach for providing different pressures across two or more sensors is illustrated with respect to FIG. 20. The illustrated embodiment depicts a first sensor 240 and a second sensor 242 positioned against the patient's forehead 16 by the headband 14. In the depicted embodiment, the first sensor 240 has a respective first contact area 244 with the patient 12, and the second sensor 242 has a respective second contact area 246 with the patient 12. The first sensor 240 also has a respective first thickness 248 and the second sensor 242 has a respective second thickness 250. In situations where the first and second contact areas 244, 246 and the first and second thicknesses 248, 250 are substantially equal, the pressure applied by the headband 14 to the first and second sensors 240, 242 may be equal. That is, the headband 14 would have the same elastic stretch over both of the sensors 240, 242, providing equal first and second respective normal forces 252, 254, depicted as arrows. Because the contact areas 244, 246 for both are also equal, equal pressures result for both sensors. While such a situation may be acceptable in situations where the first and second sensors 240, 242 are the same, it may be desirable to provide different first and second normal forces 252, 254 in embodiments where the first and second sensors 240, 242 are different.

Accordingly, in embodiments where the contact areas 244, 246 are kept substantially equal, the effective thickness of the second sensor 242 may be increased relative to the respective first thickness 248 of the first sensor 240. Thus, the elastic stretch distance or localized tension of the headband 14 over the region of the second sensor 242 may be increased, causing the second normal force 254 to increase. Thus, the pressure between the second sensor 242 and the patient's forehead 16 may be higher than the pressure between the first sensor 240 and the patient's forehead 16. In accordance with certain embodiments, the second thickness 250 of the second sensor 242 may be increased to a third thickness 255 by providing an additional layer 260 in abutment with the second sensor 242. Thus, the additional layer 260 may be configured to increase the localized stretch distance or tension of the headband 14 in the region over the second sensor 242. By way of example, the additional layer 260 may be any layer material, such as a plastic layer, a foam layer, a series of paper or cardboard sheets, adhesive layers, fabric, a gel, or another padding or rigid layer. In one embodiment, the additional layer 260 may be a material that is the same as the main material of the second sensor 242, such as a PORON® polyurethane foam available from Rogers Corporation.

Figure 21:
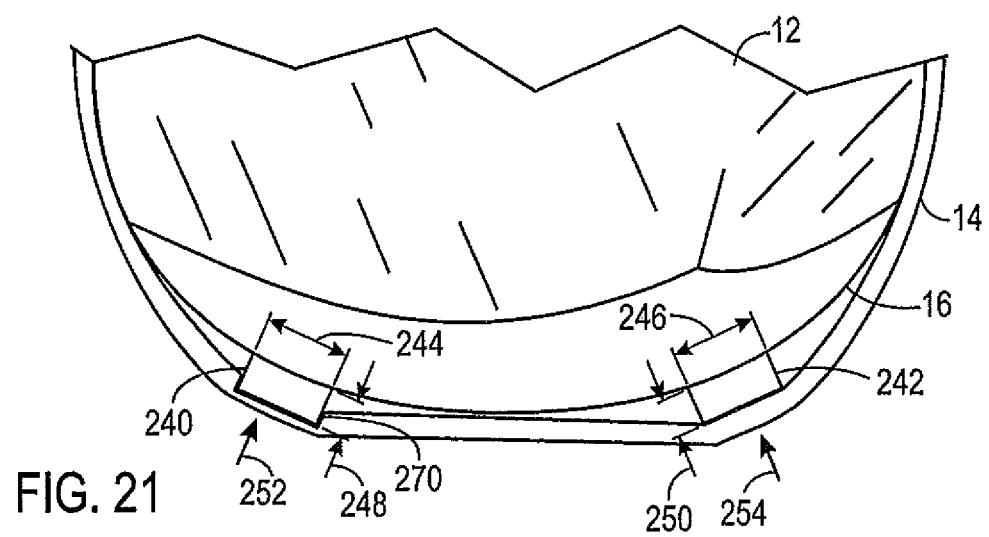
FIG. 21 is a top view of an embodiment of the headband of FIGS. 1-4 and illustrated as securing two sensors to a patient, the headband being configured to provide different pressures against the patient's forehead by providing a pocket or relief in the headband for either or both of the sensors, in accordance with an aspect of the present disclosure.

In embodiments where the headband 14 may be used with at least one particular type of sensor, the headband 14 may include certain features tailored specifically for one or both of the first and/or second sensors 240, 242. For example, as illustrated in FIG. 21, the headband 14 may include a relief or pocket 270 configured to receive the first sensor 240. The relief or pocket 270 may be sized so as to conform to the general shape of the first sensor 240 while enabling the headband 14 to provide a suitable first normal force 252 for accurate measurements when the headband 14 is adjusted to its proper tension. Thus, even in situations where the respective thicknesses 248, 250 and respective contact areas 244, 246 are substantially the same for the first and second sensors 240, 242, the local tension of the headband 14 over the first sensor 240 may be lower than the local tension of the headband 14 over the second sensor 242, reducing the first normal force 252 relative to the second normal force 254. Accordingly, the pressure of the first sensor 240 against the patient's forehead 16 may be lower than the pressure of the second sensor 242 against the patient's forehead 16. It should be noted that while the illustrated embodiment depicts the headband 14 as having only the single pocket or relief 270, other embodiments where the headband 14 includes two or more pockets or relieves are also presently contemplated. For example, the headband 14 may include the pocket or relief 270 for the first sensor 242 and a second relief for the second sensor 242, the second pocket or relief being configured to provide an appropriate second normal force 254 when the headband 14 is properly tensioned.

Figure 22:
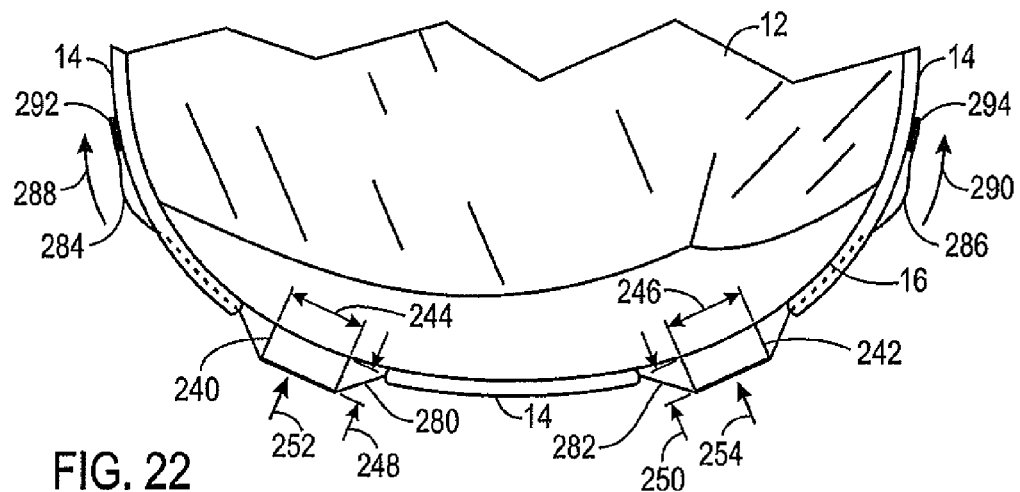
FIG. 22 is a top view of an embodiment of the headband of FIGS. 1-4 and illustrated as securing two sensors to a patient, the headband having an elastic band for each of the sensors, wherein the elastic bands are configured to provide different pressures between the sensors and the patient's forehead, in accordance with an aspect of the present disclosure.

While the embodiment described above relates to the use of the headband 14 with at least one particular type or size of sensor, other embodiments where the headband 14 may have adjustable elastic pockets for use with a variety of different sensors are also presently contemplated. For example, as illustrated in FIG. 22, the headband 14 may include first and second elastic pockets 280, 282 configured to hold the first and second sensors 240, 242, respectively. The first and second elastic pockets 280, 282 may be formed directly into the headband 14, as illustrated. In certain embodiments, the elasticity of the first and second elastic pockets 280, 282 may be different. In such embodiments, in situations where the first and second sensors 240, 242 have substantially equal sizes (i.e., thicknesses and contact areas with the patient 12), different first and second normal forces 252, 254 may be applied by the headband 14. For example, in embodiments where the first elastic pocket 280 has a higher elasticity than the second elastic pocket 282, the first normal force 252 may be lower than the second normal force 254, causing the pressure between the first sensor 240 and the patient's forehead 16 to be lower than the pressure between the second sensor 242 and the patient's forehead 16.

The first and second normal forces 252, 254 provided by the first and second elastic pockets 280, 282 may also be adjustable. For example, the first and second elastic pockets 280, 282 may each be coupled to respective first and second tensioning bands 284, 286, which may also be elastic, or may be relatively non-elastic. For example, in one embodiment, the respective first and second tensioning bands 284, 286 may be extensions of the elastic material of the first and second elastic pockets 280, 282. In other embodiments, the first and second tensioning bands 284, 286 may be made from materials similar to that of the non-elastic band 86 of FIG. 4. The first elastic pocket 280 may be tensioned by pulling the first tensioning band 284 in a general direction away from the first sensor 240, as depicted by arrow 288. Similarly, the second elastic pocket 282 may be tensioned by pulling the second tensioning band 286 in a general direction away from the second sensor 242, as depicted by arrow 290. Each of the first and second tensioning bands 284, 286 may then be secured using respective first and second closure mechanisms 292, 294. The first and second closure mechanisms 292, 294 may be HAL fasteners, hook and eye fasteners, buttons, adhesives, snaps, clips, and so forth. Indeed, the first and second closure mechanisms 292, 294 may incorporate any one or a combination of the tension setting, closure mechanism, and tension indication features described above with respect to FIGS. 8-13. Further, the headband 14 of FIG. 22 may include a variety of tension indicators, such as sensor-specific indicators that indicate proper tension settings for pulse oximetry sensors, BIS sensors, photon density wave sensors, photoacoustic sensors, and so on.

Figure 23:
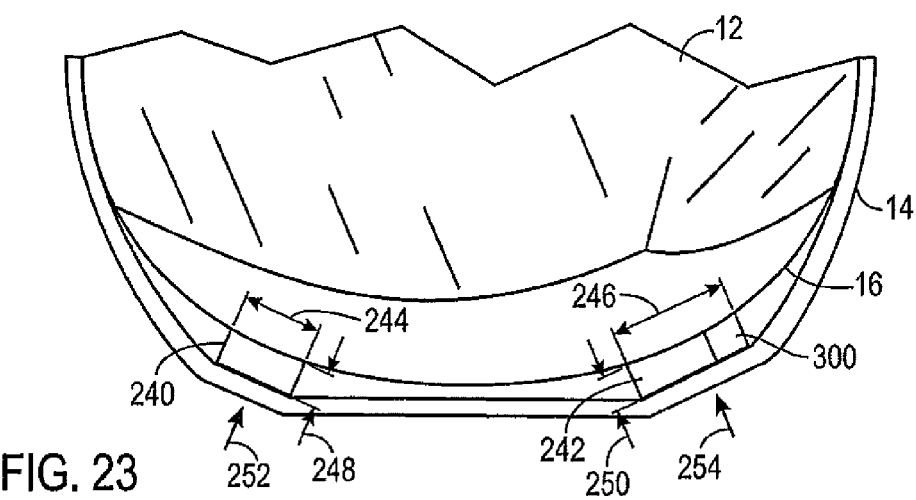
FIG. 23 is a top view of an embodiment of the headband of FIGS. 1-4 and illustrated as securing two sensors to a patient, the sensors and the headband being configured to provide different pressures against the patient's forehead by providing a different contact area between the sensors and the patient's forehead, in accordance with an aspect of the present disclosure.

In certain embodiments, it may be desirable to retain similar thicknesses 248, 250 for the first and second sensors 240, 242. Accordingly, the present disclosure also provides embodiments in which the contact areas 244, 246 for the first or second sensors 240, 242 may be adjusted. As illustrated in FIG. 23, the second sensor 242 may be configured to have a greater contact area 246 than the contact area 244 of the first sensor 240. Accordingly, in embodiments where the normal forces 252, 254 are substantially the same, the pressure between the second sensor 242 and the patient's forehead 16 will be lower than the pressure between the first sensor 240 and the patient's forehead 16. The contact area 246 of the second sensor 242 may be increased, for example, using an additional layer 300 disposed against the second sensor 242. In some embodiments, the additional layer 300 may have substantially the same thickness 250 as the second sensor 242, and, in certain of these embodiments, may be adhesively secured to the second sensor 242 to create the contact area 246.

Figure 24:
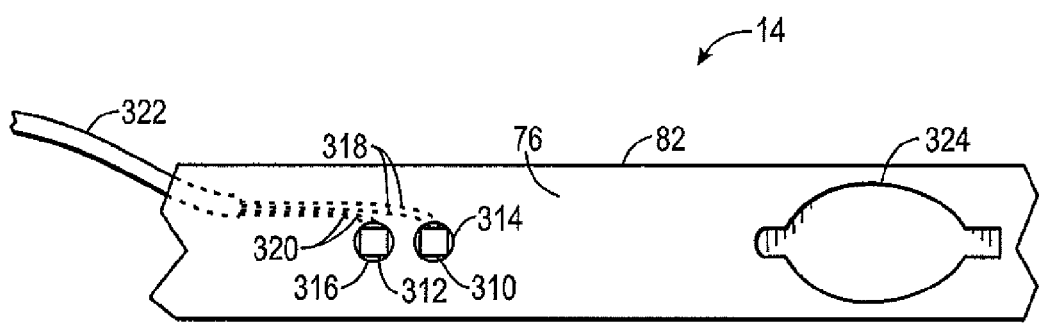
FIG. 24 is a front view of the inner surface of an embodiment of the headband of FIGS. 1-4, the headband having integrated components for performing physiological measurements and also having a receptacle for a sensor, in accordance with an aspect of the present disclosure.

In addition to or in lieu of the embodiments described above relating to tension setting, reducing headband slippage, and/or providing equal or different pressures across multiple sensors, as illustrated in FIG. 24 the present disclosure also provides embodiments for integrating a medical sensor, such as the sensor 10, with the headband 14. The sensor 10 may be integrated with the headband 14 such that the main headband portion 82 serves as the body 20 of the sensor 10, or such that the body 20 of the sensor 10 may be housed within the main headband portion 82, or, as illustrated, a combination thereof. Indeed, the embodiment of the headband 14 illustrated in FIG. 24 may also be configured to provide the same or different pressures across multiple sensors, as described above.

Thus, the headband 14 illustrated in FIG. 24 may include sensing components, such as an emitter 310 and a detector 312, which may be placed directly onto the inner surface 76 of the headband 14, or inside the headband 14. In one embodiment, the emitter 310 and the detector 312 may be configured to perform pulse oximetry measurements. In embodiments where the emitter 310 and the detector 312 are inside of the headband 14, the main headband portion 82 may include respective openings 314, 316, corresponding to the desired positioning of the emitter 310 and the detector 312, respectively. Further, as illustrated, a first set of conductors 318 and a second set of conductors 320, which are configured to shuttle signals to and from the emitter 310 and the detector 312, respectively, may be disposed within the main headband portion 82. As illustrated with respect to FIG. 2, a cable 322 may be routed to the outer surface 32 of the headband 14, rather than between the inner surface 76 of the headband 14 and the patient 12. It should be noted that the first and second set of conductors 318, 320 may include conductive wires, light conductors (e.g., optical fibers), or similar materials. Indeed, the headband 14 in accordance with the present embodiment may incorporate any of the sensor approaches described in U.S. application Ser. No. 12/722,355 filed on Mar. 11, 2010, entitled "MEDICAL SENSOR WITH FLEXIBLE COMPONENTS AND TECHNIQUE FOR USING THE SAME," which is hereby incorporated by reference in its entirety for all purposes.

Additionally or alternatively, the headband 14 may include a sensor opening 324, which is configured to receive and hold a sensor having a desired size, shape, or configuration. By way of example, the embodiment illustrated in FIG. 24 depicts the sensor opening 324 as having a shape and size so as to conform to the sensor 10 depicted in FIGS. 1-3. However, the sensor opening 324 may be configured to hold any medical sensor, such as a BIS sensor, a photon density wave sensor, a photoacoustic sensor, and so on. The sensor opening 324 may be configured to support the sensor 10 within the main headband portion 82 to limit movement of the sensor 10 relative to the headband 14. Further, the positioning of the sensor 10 within the headband 14 also enables alternatives to adhesives to be used to secure the sensor 10 to the patient 12. For example, the body 20 of the sensor 10 discussed with respect to FIG. 1 may have a rubber or similar surface configured to have a relatively large coefficient of friction with the patient's skin.

As noted above with respect to FIG. 2, the cable 26 of the sensor 10 may also be routed to the outer surface 32 of the headband 14, which may enhance the comfort of the patient 12. However, embodiments where either or both cables 26, 322 are routed between the headband 14 and the patient 12 are also presently contemplated. In such embodiments, it may be desirable to configure the cables 26, 322 to have a flat surface configured to be placed against the patient 12.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A headband, comprising:
   a main headband portion comprising a first end and a second end, the main headband portion being adapted to wrap around the circumference of a patient's head;
   a first additional band coupled to the main headband portion and adapted to secure the headband to a top or a back portion of the patient's head, wherein the first additional band and the main headband portion are configured to reduce movement of the headband in relation to the patient's head;
   a closure mechanism adapted to couple the first end with the second end of the main headband portion; and
   a tensioning mechanism coupling the closure mechanism with the main headband portion and adapted to vary a normal force provided by the headband against a medical sensor secured to the patient's head;
   wherein the headband is configured to relax over a first distance after initially securing the first end to the second end at a first tension setting of the tensioning mechanism, the first tension setting being outside of a desired tension range defined by a tension range indicator on the main headband portion, and the relaxation over the first distance is sufficient to de-tension the headband from the first tension setting of the tensioning mechanism to a second tension setting within the desired tension range.

2. The headband of claim 1, comprising a second additional band secured to the main headband portion and configured to secure the headband to the back portion of the patient's head, wherein the first additional band is configured to secure the headband to the top portion of the patient's head.

3. The headband of claim 2, wherein the first and second additional bands each comprise a respective ends that is stitched to the main headband portion, and the first and second bands are adapted to move in a crosswise direction relative to the circumference of the patient's head.

4. The headband of claim 2, wherein the first and second additional bands each comprise a respective end that is coupled to the main headband portion via a mechanical pivot joint adapted to enable radial movement of the first and second additional bands relative to the main headband portion.

5. The headband of claim 1, wherein the tensioning mechanism comprises:
   an elastic band coupling the main headband portion with the closure mechanism, wherein the elastic band is configured to evenly stretch along the first end to tension the headband as the closure mechanism is pulled in a direction generally away from the first end; and
   a hard stop formed by an abutment surface of the elastic band and a loop disposed between the abutment surface and the closure mechanism, wherein the loop is configured to contact the abutment surface of the elastic band to prevent the elastic band from any further substantial amount of stretching such that the hard stop defines a maximum tension setting of the tensioning mechanism.

6. The headband of claim 5, wherein the maximum tension setting is greater than the desired tension range for applying a desired amount of pressure between a medical sensor and the patient's forehead.

7. The headband of claim 5, comprising a low friction material that enables the elastic band to evenly stretch along the first end as the closure mechanism is pulled in a direction generally away from the first end.

8. The headband of claim 7, wherein the low friction material comprises a low friction strip disposed between the main headband portion and the elastic band, wherein the low friction strip is adapted to prevent the elastic band from catching or sticking to the main headband portion as the closure mechanism is pulled in the direction generally away from the first end.

9. The headband of claim 8, wherein the low friction material comprises at least one of a fluoropolymer, high density polyethylene, or a silicone-coated film.

10. The headband of claim 1, wherein the main headband portion comprises first and second relieves or pockets adapted to hold a first medical sensor and a second medical sensor, respectively, and the headband is configured to apply a different normal force to the first medical sensor compared to the second medical sensor.

11. The headband of claim 10, wherein the first and second relieves or pockets comprise first and second elastic pockets adapted to hold first and second medical sensors, respectively, and the first elastic pocket is adapted to provide a first normal force against the first medical sensor, and the second elastic pocket is adapted to provide a second normal force against the second medical sensor, the first and second normal forces being different.

12. The headband of claim 11, wherein a first elasticity of the first elastic pocket is different from a second elasticity of the second elastic pocket.

13. The headband of claim 11, wherein the first and second elastic pockets are coupled to respective first and second tension adjustment bands, wherein the first tension adjustment band is configured to adjust a first tension of the first elastic pocket to vary the first normal force, and the second tension adjustment band is configured to adjust a second tension of the second elastic pocket to vary the second normal force.

14. The headband of claim 1, wherein the tensioning mechanism comprises an elastic band coupling the main headband portion with the closure mechanism, wherein the elastic band is configured to stretch along the first end to tension the headband as the closure mechanism is pulled in a direction generally away from the first end, and wherein the headband comprises a clip fastened to the elastic band and adapted to create folds in the elastic band to increase the stretch resistance of the elastic band, and the clip is configured to de-tension the elastic band when removed such that the headband is de-tensioned from the first tension to the second tension setting.

15. The headband of claim 1, wherein the main headband portion comprises a microporous material adapted to maintain friction between the patient's head and the headband by enabling moisture evaporation through the headband while preventing moisture absorption.

16. The headband of claim 1, comprising a gripping material secured to an inner surface of the main headband portion and adapted to increase friction between the headband and the patient's head.

17. The headband of claim 1, wherein the headband comprises a non-elastic material to prevent stretching of the main headband portion.

18. The headband of claim 1, wherein the closure mechanism is configured to enable the headband to relax over the first distance.

19. The headband of claim 18, wherein the closure mechanism comprises a hook portion that forms a hook and loop fastener with a material of the main headband portion, and the hook portion comprises a plurality of hooks, wherein a density of the plurality of hooks is such that when the headband is tensioned to the first tension setting, the hook and loop fastener allows the headband to relax over the first distance to the second tension setting.

* * * * *